(12) United States Patent
Yamaya

(10) Patent No.: US 7,670,285 B2
(45) Date of Patent: Mar. 2, 2010

(54) ENDOSCOPE TREATMENT INSTRUMENT STOPPER AND TREATMENT INSTRUMENT STOPPER SECTION

(75) Inventor: Koji Yamaya, Tokyo (JP)

(73) Assignee: Olympus Corporation, Tokyo (JP)

( * ) Notice: Subject to any disclaimer, the term of this patent is extended or adjusted under 35 U.S.C. 154(b) by 85 days.

(21) Appl. No.: 11/453,107

(22) Filed: Jun. 14, 2006

(65) Prior Publication Data
US 2006/0235356 A1    Oct. 19, 2006

Related U.S. Application Data

(63) Continuation of application No. PCT/JP04/16308, filed on Nov. 4, 2004.

(30) Foreign Application Priority Data

Dec. 18, 2003 (JP) ............................. 2003-421277
Feb. 16, 2004 (JP) ............................. 2004-038857

(51) Int. Cl.
*A61B 1/00* (2006.01)
*A61B 1/12* (2006.01)

(52) U.S. Cl. ...................... 600/154; 600/159

(58) Field of Classification Search .............. 600/106, 600/154, 159; 604/167.01–167.06, 256
See application file for complete search history.

(56) References Cited

U.S. PATENT DOCUMENTS 4,270,525 A * 6/1981 Furihata .................... 600/159
4,653,477 A * 3/1987 Akui et al. .................. 600/154
4,715,360 A   12/1987 Akui et al.
5,104,379 A * 4/1992 Nakamura et al. .......... 604/111
5,147,305 A * 9/1992 Nakamura et al. .......... 604/110
5,413,561 A * 5/1995 Fischell et al. .......... 604/167.01
6,036,672 A * 3/2000 Allen et al. ............. 604/167.02
6,117,070 A * 9/2000 Akiba ....................... 600/154

FOREIGN PATENT DOCUMENTS

| JP | HEI 3-101908 U | 10/1991 |
| JP | 06-189899 | 7/1994 |
| JP | 2001-231748 | 8/2001 |
| JP | 2003-220024 | 8/2003 |

* cited by examiner

*Primary Examiner*—Linda C Dvorak
*Assistant Examiner*—Alireza Nia
(74) *Attorney, Agent, or Firm*—Scully, Scott, Murphy & Presser, P.C.

(57) ABSTRACT

An endoscope treatment instrument stopper fitted in a channel opening of a treatment instrument insertion channel of an endoscope, includes a first stopper section having a first treatment instrument insertion hole into which a treatment instrument is inserted; a stopper frame having a stopper section fitting portion, fitted in the channel opening, having therein the first treatment instrument insertion hole of the first stopper section to be opposite the channel opening, and provided with a tearing capable of tearing the stopper frame removed from the channel opening; and a second stopper section having a second treatment instrument insertion hole into which the treatment instrument is inserted, removable from the stopper section fitting portion of the stopper frame, and formed so that the second treatment instrument insertion hole is opposite the first stopper section when the second stopper section is fitted in the stopper section fitting portion.

5 Claims, 14 Drawing Sheets

ENDOSCOPE TREATMENT INSTRUMENT STOPPER AND TREATMENT INSTRUMENT STOPPER SECTION

CROSS-REFERENCE TO RELATED APPLICATIONS

This application is a continuation of PCT international application Ser. No. PCT/JP2004/16308 filed Nov. 4, 2004 which designates the United States, incorporated herein by reference, and which claims the benefit of priority from Japanese Patent Applications No. 2003-421277, filed Dec. 18, 2003; and No. 2004-038857, filed Feb. 16, 2004, incorporated herein by reference.

BACKGROUND OF THE INVENTION

1. Field of the Invention

The present invention relates to an endoscope treatment instrument stopper which is fitted in a channel opening of a treatment instrument insertion channel provided in an endoscope and inserts in an air-tight manner a treatment instrument from the treatment instrument insertion channel opening into the treatment instrument insertion channel and to a treatment instrument stopper section forming the endoscope treatment instrument stopper.

2. Description of the Related Art

Conventionally, in observation and treatment in a body cavity using an endoscope, a liquid medicine is injected into the body cavity from a treatment instrument insertion channel provided in the endoscope and a treatment instrument is inserted thereinto to cut and extract a diseased portion.

In the treatment using an endoscope, contaminants and air in the body cavity can be flowed backward through the treatment instrument insertion channel due to changes in pressure in the body cavity to be leaked out to the outside from the channel opening of the treatment instrument insertion channel. A stopper section is fitted in the channel opening of the treatment instrument insertion channel of the endoscope to prevent the contaminants and air flowed backward through the treatment instrument insertion channel from being leaked out.

The stopper section fitted in the channel opening of the treatment instrument insertion channel is of a reuse type which can be reused by being cleaned and sterilized after use or of a disposal type which cannot be reused by collapsing the stopper section fitted in the channel opening of the treatment instrument insertion channel for use when removed from the channel opening.

The reuse type stopper section must be cleaned and sterilized for each use. Its cleaning and sterilization management is troublesome. The disposal type stopper section is preferred. The disposal type stopper section, as proposed in Japanese Utility Model Application Laid-Open (JP-U) No. H03-101908, has a stopper body formed of an elastic member and including an upper stopper body and a lower stopper body, a stopper frame formed of a member relatively harder than that of the stopper body and housing and holding the stopper body, an engagement portion formed in the stopper frame and engaging the stopper frame to a channel opening of a treatment instrument insertion channel, a tearing formed in the stopper frame and tearing the stopper frame by a force when the stopper section is removed from the channel opening, and an opening unit formed in the stopper frame to be connected to the tearing.

SUMMARY OF THE INVENTION

An endoscope treatment instrument stopper according to one aspect of the present invention is fitted in a channel opening of a treatment instrument insertion channel of an endoscope, and includes a first stopper section having a first treatment instrument insertion hole into which a treatment instrument is inserted; a stopper frame having a stopper section fitting portion, fitted in the channel opening, having therein the first treatment instrument insertion hole of the first stopper section to be opposite the channel opening, and provided with a tearing capable of tearing the stopper frame removed from the channel opening; and a second stopper section having a second treatment instrument insertion hole into which the treatment instrument is inserted, removable from the stopper section fitting portion of the stopper frame, and formed so that the second treatment instrument insertion hole is opposite the first stopper section when the second stopper section is fitted in the stopper section fitting portion.

An endoscope treatment instrument stopper according to another aspect of the present invention includes a stopper frame having a tearing tearable when the stopper frame is removed from a channel opening of a treatment instrument insertion channel of an endoscope; and a stopper section having a treatment instrument insertion path into which a treatment instrument is inserted and a handle, and fitted to be removable from the stopper frame. The stopper frame has a tab for removing the stopper frame provided in a position where a distance from the channel opening to the tab is shorter than that from the channel opening to the handle in a state where the stopper section is fitted in the stopper frame and the stopper frame is fitted in the channel opening.

A treatment instrument stopper section according to still another aspect of the present invention forms an endoscope treatment instrument stopper together with a predetermined stopper frame fitted in a channel opening of a treatment instrument insertion channel of an endoscope, and includes a removal unit removable from a stopper section fitting portion provided in the stopper frame and having a treatment instrument insertion hole into which a treatment instrument is inserted when the removal unit is fitted in the stopper section fitting portion; and a coupling segment having an attachment part fixed to a portion other than the stopper section fitting portion of the stopper frame and exerting the removal unit in a direction moved away from the stopper section fitting portion when the removal unit is removed from the stopper section fitting portion.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention will be described below in detail with reference to the drawings.

Figure 1:
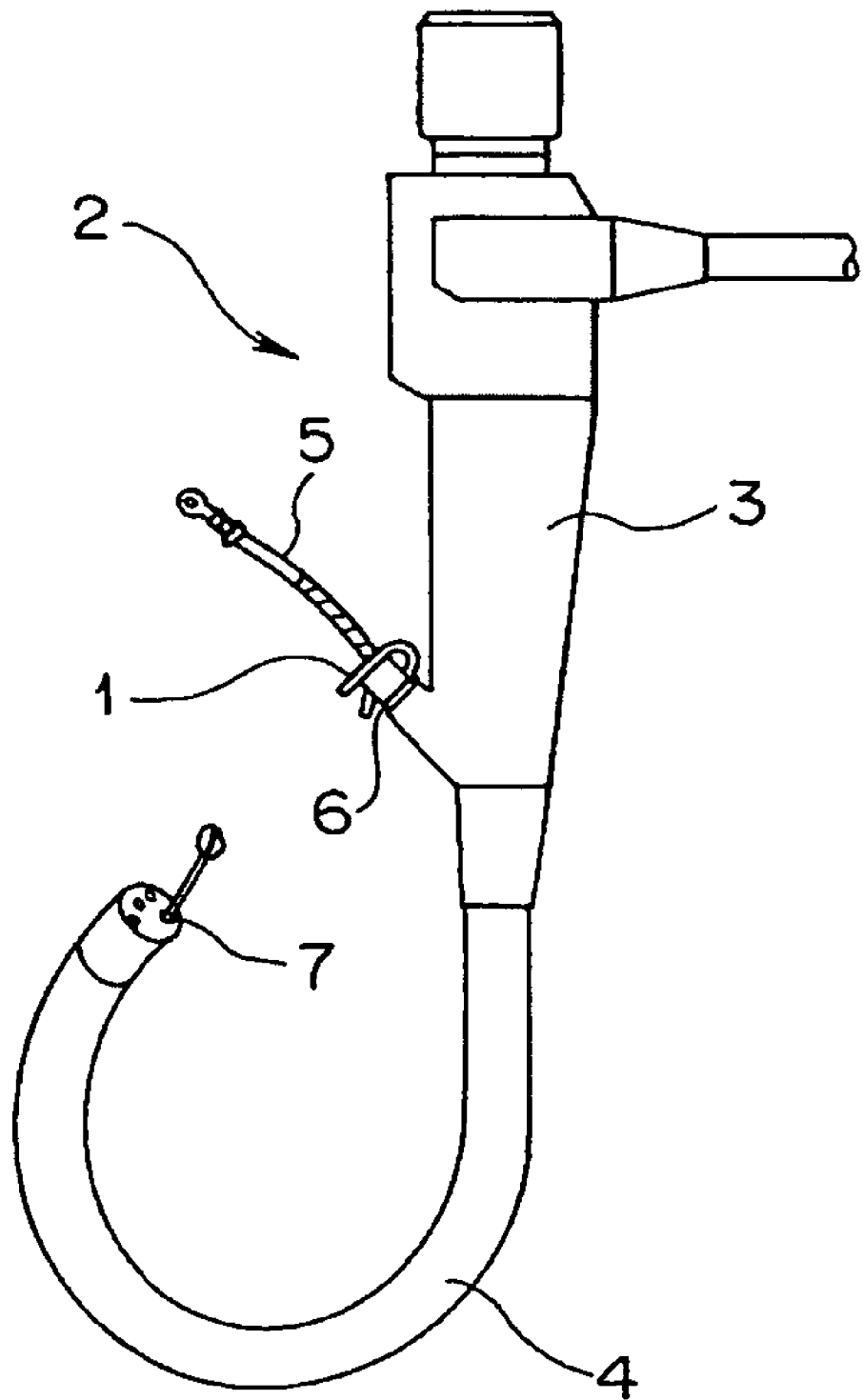
FIG. 1 is a front view of an endoscope using an endoscope treatment instrument stopper according to the present invention.
Figure 2:
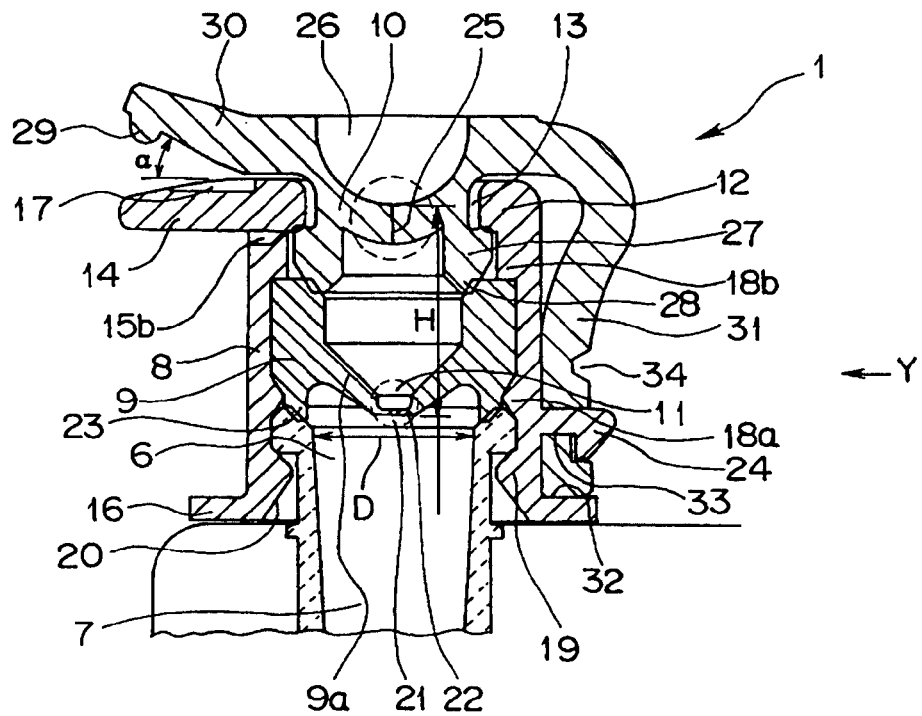
FIG. 2 is a cross-sectional view showing the state where a treatment instrument stopper according to a first embodiment of the endoscope treatment instrument stopper according to the present invention is fitted in a channel opening of a treatment instrument insertion channel.
Figure 3:
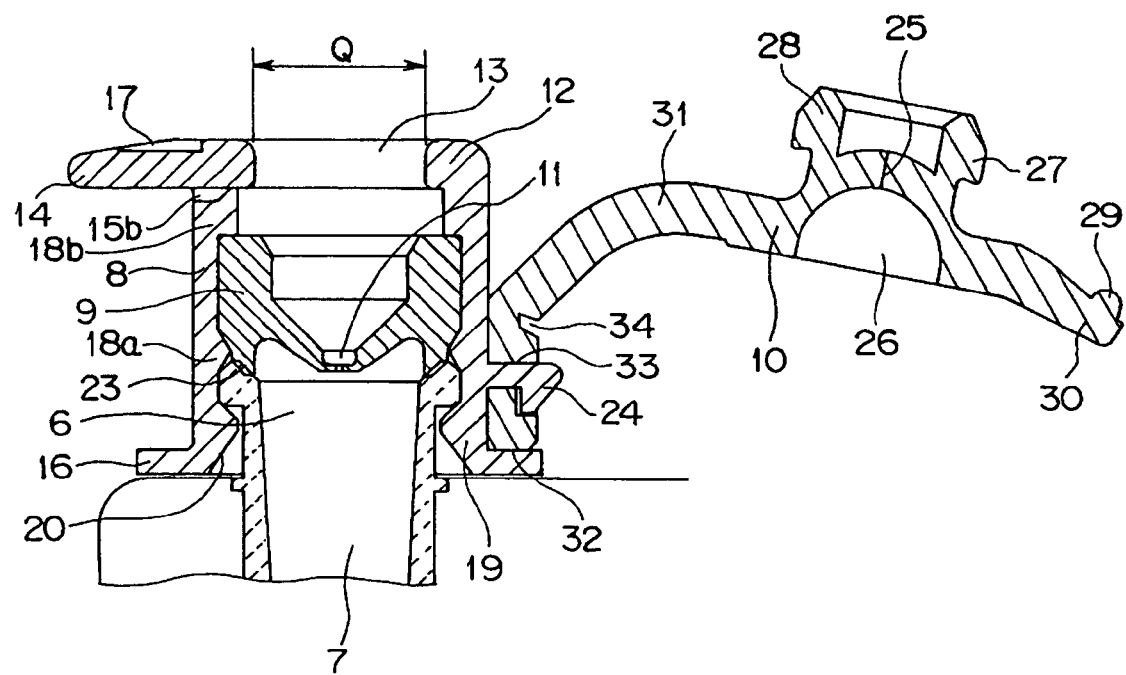
FIG. 3 is a cross-sectional view showing the state where a second stopper section of the treatment instrument stopper according to the first embodiment of the endoscope treatment instrument stopper according to the present invention is removed from the state of FIG. 1.
Figure 4:
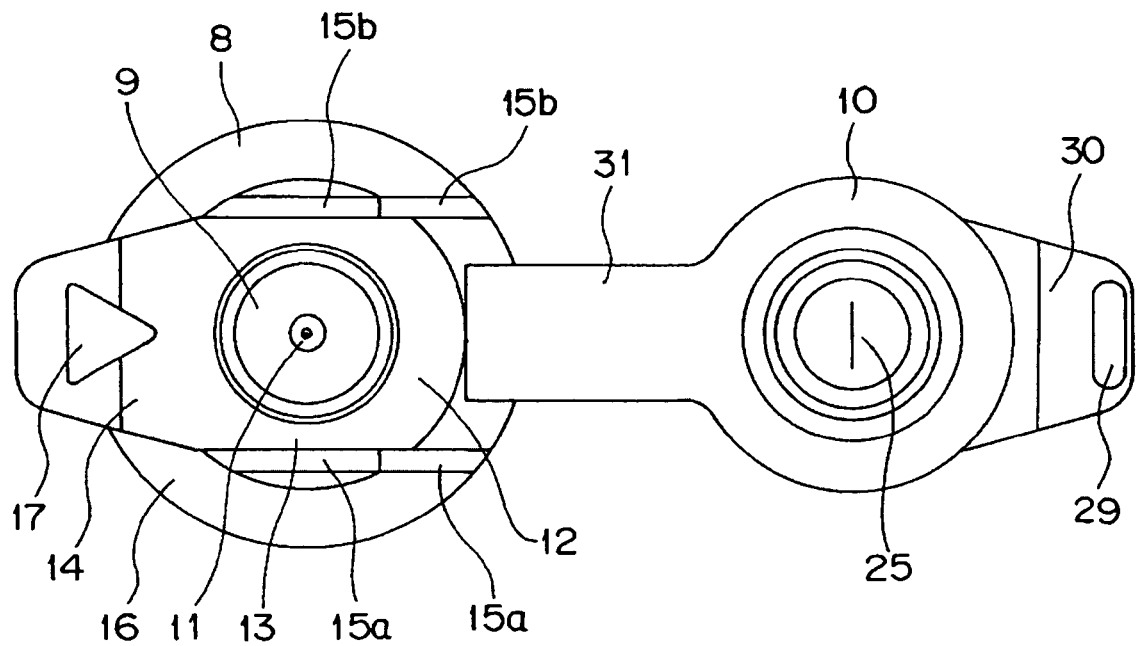
FIG. 4 is a top view of the treatment instrument stopper according to the first embodiment of the endoscope treatment instrument stopper according to the present invention shown in FIG. 2, seen from top.
Figure 5:
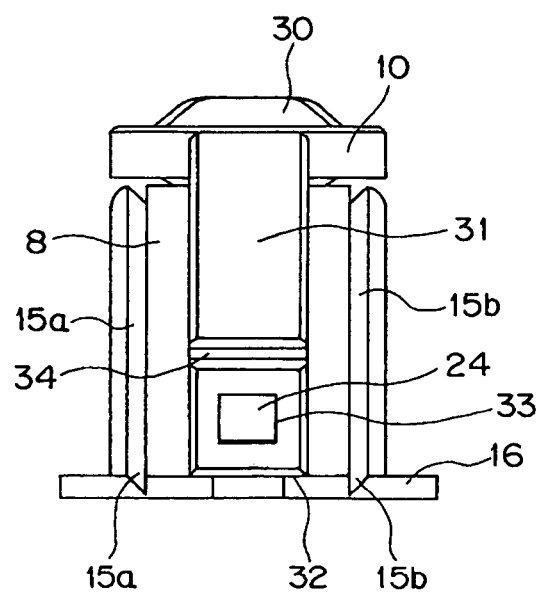
FIG. 5 is a side view of the treatment instrument stopper according to the first embodiment of the endoscope treatment instrument stopper according to the present invention shown in FIG. 1, seen in the direction of arrow Y in the drawing.
Figure 6:
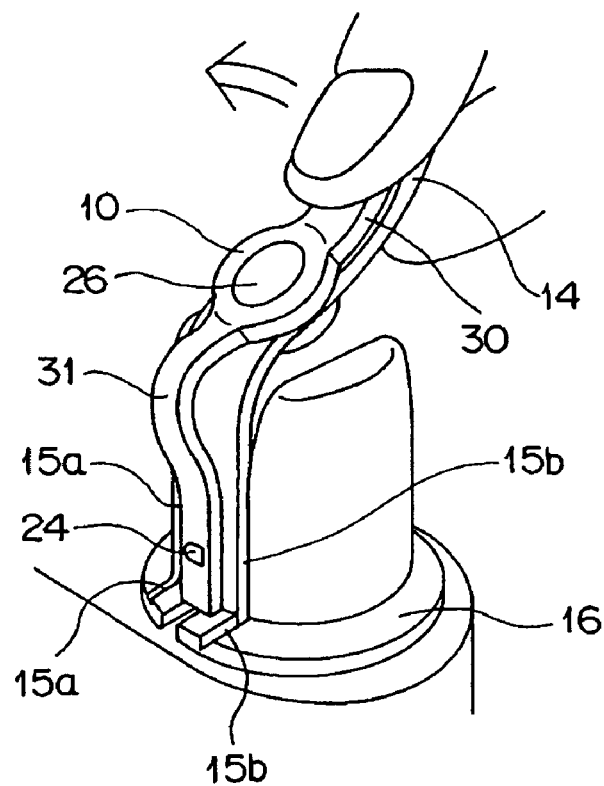
FIG. 6 is a perspective view showing the state of operating the second stopper section of the treatment instrument stopper according to the first embodiment of the endoscope treatment instrument stopper according to the present invention.
Figure 7:
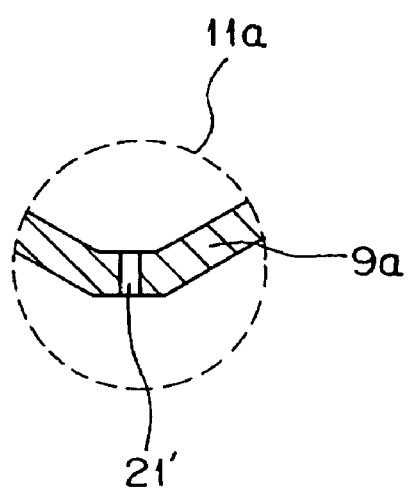
FIG. 7 is a cross-sectional view showing a first modification example of a first stopper section of the treatment instrument stopper according to the first embodiment of the endoscope treatment instrument stopper according to the present invention.
Figure 8:
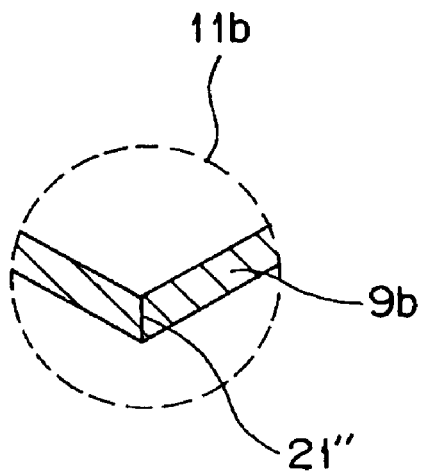
FIG. 8 is a cross-sectional view showing a second modification example of the first stopper section of the treatment instrument stopper according to the first embodiment of the endoscope treatment instrument stopper according to the present invention.
Figure 9:
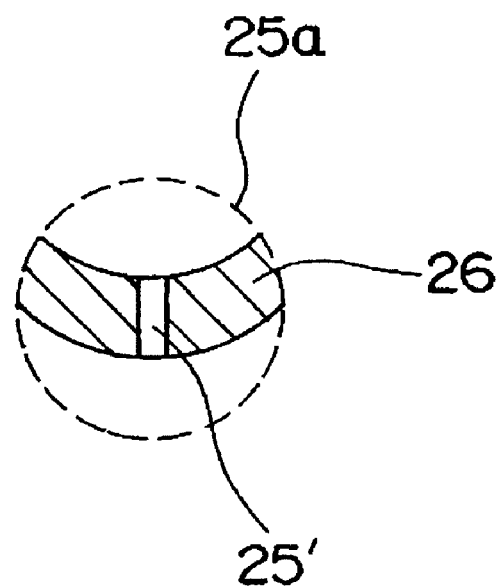
FIG. 9 is a cross-sectional view showing a first modification example of the second stopper section of the treatment instrument stopper according to the first embodiment of the endoscope treatment instrument stopper according to the present invention.

A first embodiment of an endoscope treatment instrument stopper according to the present invention will be described using FIGS. 1 to 9. FIG. 1 is a front view of an endoscope using an endoscope treatment instrument stopper according to the present invention; FIG. 2 is a cross-sectional view showing the state where a treatment instrument stopper according to the first embodiment of the endoscope treatment instrument stopper according to the present invention is fitted in a channel opening of a treatment instrument insertion channel; FIG. 3 is a cross-sectional view showing the state where a second stopper section of the treatment instrument stopper according to the first embodiment of the endoscope treatment instrument stopper according to the present invention is removed from the state of FIG. 2; FIG. 4 is a top view of the treatment instrument stopper according to the first embodiment of the endoscope treatment instrument stopper according to the present invention shown in FIG. 3, seen from top; FIG. 5 is a side view of the treatment instrument stopper according to the first embodiment of the endoscope treatment instrument stopper according to the present invention shown in FIG. 2, seen in the direction of arrow Y in the drawing; FIG. 6 is a perspective view showing the state of operating the second stopper section of the treatment instrument stopper according to the first embodiment of the endoscope treatment instrument stopper according to the present invention; FIG. 7 is a cross-sectional view showing a first modification example of a first stopper section of the treatment instrument stopper according to the first embodiment of the endoscope treatment instrument stopper according to the present invention; FIG. 8 is a cross-sectional view showing a second modification example of the first stopper section of the treatment instrument stopper according to the first embodiment of the endoscope treatment instrument stopper according to the present invention; FIG. 9 is a cross-sectional view showing a first modification example of the second stopper section of the treatment instrument stopper according to the first embodiment of the endoscope treatment instrument stopper according to the present invention.

First, an endoscope using an endoscope treatment instrument stopper according to the present invention will be described using FIG. 1. An endoscope 2 has an operation unit 3 held by the operator, and an insertion unit 4 which is long and has flexibility. The operation unit 3 has a channel opening 6 for inserting a treatment instrument 5 such as a forceps or various treatment instruments into a treatment instrument insertion channel, a universal cable, not shown, incorporating a light guide connected to a light source, a bending operation knob, not shown, remotely bending a bendable portion provided in the end of the insertion unit 4, and a water and air supply venting cap, not shown, connecting a water and air supply pump. The channel opening 6 of the operation unit 3 is fitted with a later-described treatment instrument stopper 1 according to the present invention. The treatment instrument stopper 1 holds air-tight properties between the treatment instrument insertion channel and the outside when the treatment instrument 5 is inserted and removed.

The insertion unit 4 has a proximal end connected to the operation unit 3 and a distal end having a distal end portion and a bendable portion. A treatment instrument insertion channel 7 communicated with the channel opening 6 of the operation unit 3 is provided on the end surface of the distal end portion of the insertion unit 4. The treatment instrument 5 is inserted from the channel opening 6 into the treatment instrument insertion channel 7 to be drawn out from the end surface of the distal end portion. The light guide and the water and air supply channel are provided in the insertion unit 4 and are communicated with the end surface of the distal end portion.

The endoscope treatment instrument stopper according to the present invention will be described using FIGS. 2 to 5. The treatment instrument stopper 1 has a stopper frame 8 formed of a plastic material such as polyethylene having slight elasticity, a first stopper section 9 formed of a material such as silicon rubber having elasticity greater than that of the stopper frame 8, and a second stopper section 10 formed of a material such as silicon rubber. The stopper frame 8 and the second stopper section 10 are formed of members independent from each other. The stopper frame 8 is formed of a material harder than that of the second stopper section 10.

The stopper frame 8 is formed in a substantially cylindrical shape having an upper end wall 12. The upper end wall 12 is provided with a stopper section fitting portion 13 from which the later-described second stopper section 10 is removed. The upper end wall 12 has one end formed integrally with a tab 14 extended sideward of the stopper frame 8.

Protruded retaining portions 18a and 18b for fitting and retaining the outer circumference of the later-described first stopper section 9 are circumferentially or partially formed on the inner circumference surface of the cylindrical middle portion of the stopper frame 8. A protruded engagement portion 19 for fitting the stopper frame 8 in the channel opening 6 of the treatment instrument insertion channel 7 of the endoscope 2 is circumferentially or partially formed on the inner circumference surface at the lower end of the stopper frame 8.

The protruded engagement portion 19 has a tilted surface 20 on the opening side at the lower end of the stopper frame 8. The engagement portion 19 can press fit the stopper frame 8 to the outer circumference of the channel opening 6 by the tilted surface 20.

When the stopper frame 8 is pressed into the channel opening 6, the engagement portion 19 can engage the stopper frame 8 with the channel opening 6 beyond a flanged mouth thereof by the tilted surface 20. When the engagement portion 19 is once engaged, the stopper frame 8 cannot be removed from the channel opening 6. The shape of the engagement portion 19 and the mouth shape of the channel opening 6 are not limited to those of this embodiment. Any shape in which the stopper frame 8 can be easily fitted in the channel opening 6 and the fitted stopper frame 8 cannot be removed from the channel opening 6 may be used.

A flange 16 is extended from the outer circumference at the lower end of the stopper frame 8 to be in substantially parallel with the tab 14. The stopper frame 8 is provided with an attachment part 24 for attaching the later-described second stopper section 10 to the outside surface on the lower end side opposite the tab 14. The tab 14 provided on the upper end wall 12 of the stopper frame 8, as shown in FIG. 4, can be held by the operator and is formed to have a width smaller than the cylindrical outer diameter of the stopper frame 8.

The upper end wall 12, as shown in FIG. 4, is provided with a tearing including a pair of notched grooves 15a and 15b. The notched grooves 15a and 15b as the tearing are formed at a pitch substantially equal to the width of the tab 14 and are extended to the cylindrical outside of the stopper frame 8 and the flange 16 opposite the tab 14. When the tab 14 is pulled up, the notched grooves 15a and 15b are formed so that the stopper frame 8 can be easily torn from the notched grooves 15a and 15b. The attachment part 24, as shown in FIG. 5, is formed between the notched grooves 15a and 15b provided on the outside of the stopper frame 8.

The notched groove shape of the tearing including the notched grooves 15a and 15b may be V- or U-shaped to be formed to be thinner than other portions or may be in a dashed line shape, thereby being easily torn by the tab 14. Any shape construction may be used.

The notched grooves 15a and 15b, as shown in FIGS. 2 and 3, may be provided on the base side of the tab 14 or openings may be provided on the base side of the tab 14. They may be easily torn by a small pullup force. An index 17 indicating a pullup direction is provided on the upper surface of the tab 14.

The first stopper section 9 has a cylindrical outer shape and is provided at the lower end of the cylindrical inner circumference with a first closed film 9a formed in a substantially funnel shape. The center portion of the first closed film 9a has a first treatment instrument insertion hole 11. The first treatment instrument insertion hole 11 has a small hole 21 and a thin wall 22. When the treatment instrument 5 is inserted into the first treatment instrument insertion hole 11, the treatment instrument 5 deforms and extends the small hole 21 and the thin wall 22.

The first stopper section 9 has an outside formed to have a geometry in which it is fitted and retained between the retaining portions 18a and 18b of the stopper frame 8. The first stopper section 9 is inserted from the lower end opening of the stopper frame 8 to be brought into contact with the retaining portion 18b beyond the engagement portion 19 and the retaining portion 18a provided on the inner circumference surface of the stopper frame 8 and is fitted between the retaining portions 18a and 18b. The assembling operation inserting and fitting the first stopper section 9 into the stopper frame 8 is a simple one-way pressing operation and can easily realize automatic assembling by machining. The lower end of the first stopper section 9 is provided with a first seal 23 contacted in a water-tight manner with the circumference of the mouth of the channel opening 6 fitted with the stopper frame 8.

A first treatment instrument insertion hole 11a provided in the first closed film 9a of the first stopper section 9, as shown in FIG. 7, may be a small hole 21' having the same diameter holed to be communicated with the upper and lower sides of the first closed film 9a, or, as shown in FIG. 8, may be a slit 21" holed to be communicated with the upper and lower sides of the first closed film 9b. A first treatment instrument insertion hole 11b is formed to be a shape in which the first closed film 9b is contacted with the outer circumference of the inserted treatment instrument.

The second stopper section 10 has a removal unit 27 in a substantially cylindrical shape fitted in the stopper section fitting portion 13 provided in the upper end wall 12 of the stopper frame 8, a handle 30 extended from the upper surface side of the removal unit 27, and a coupling segment 31 opposite the handle 30 to be extended from the upper surface side of the removal unit 27, which are integrally formed.

The upper side opening of the removal unit 27 of the second stopper section 10 is provided with a hemispherical second closed film 26. The center of the hemispherical second closed film 26 is provided with a second treatment instrument insertion hole 25 formed in a slit communicated with the upper and lower sides of the second closed film 26. The second treatment instrument insertion hole 25 may be a slit, or, as shown in FIG. 9, may be a small hole 25' having the same diameter holed to be communicated with the upper and lower sides of the second closed film 26. The second treatment instrument insertion hole 25 is formed to be a shape in which the second closed film 26 is contacted with the outer circumference of the inserted treatment instrument.

The lower opening end of the removal unit 27 of the second stopper section 10 is provided with a second seal 28 contacted in a water-tight manner with the periphery of the upper opening of the first stopper section 9 when the removal unit 27 is fitted in the stopper section fitting portion 13 of the stopper frame 8.

The handle 30 of the second stopper section 10 is provided in the position in which it is overlapped with the top surface portion of the tab 14 of the stopper frame 8 when the removal unit 27 of the second stopper section 10 is fitted in the stopper frame 8. The handle 30 has a shape substantially equal to that of the tab 14 and a surface opposite the tab 14 provided with a convex 29, and is formed to be tilted upward at an angle α with respect to the upper surface of the tab 14 in the drawing. The handle 30 has a tilt at the angle α and has the convex 29. The handle 30 can be easily held and pulled up by the operator. The tilt angle α of the handle 30 is desirably about 20°.

The coupling segment 31 of the second stopper section 10 is formed in a belt shape on the side opposite the handle 30 and has a distal end provided with a mounting hole 33 fitted in the attachment part 24 provided on the outer surface (the side surface) of the stopper frame 8 so as to be arranged in parallel between the notched grooves 15a and 15b of the stopper frame 8. A part (the mounting hole 33) of the coupling segment 31 is fixed on the outer surface of the stopper frame 8 via the attachment part 24. The coupling segment 31 near the position provided with the mounting hole 33 is provided with a hinge 34 for hanging the second stopper section 10 removed from the stopper frame 8 in the position away from the insertion periphery of the stopper section fitting portion 13 of the stopper frame 8. The end surface of the coupling segment 31 is provided with a planar portion 32 to be brought into contact with the flange 16 of the stopper frame 8.

The mounting hole 33 of the coupling segment 31 of the second stopper section 10 is fitted in the attachment part 24 of the stopper frame 8. The removal unit 27 of the second stopper section 10 having the coupling segment 31 attached to the stopper frame 8 is inserted into the stopper section fitting portion 13 of the stopper frame 8. The periphery of the upper opening of the first stopper section 9 held in the inner circumstance of the stopper frame 8 is contacted in a water-tight manner with the second seal 28 of the second stopper section 10.

When the second stopper section 10 is removed from the stopper frame 8 in this state and the handle 30 is held and pulled up, the removal unit 27 can be removed from the stopper section fitting portion 13 of the stopper frame 8, the removed second stopper section 10 is hung from the hinge 34 along the outside of the stopper frame 8. Rotation and falling of the coupling segment 31 can be prevented by the planar portion 32 in the distal end portion.

Assembling of the treatment instrument stopper 1 including the stopper frame 8, the first stopper section 9, and the second stopper section 10 and fitting of the treatment instrument stopper 1 in the channel opening 6 of the treatment instrument insertion channel 7 will be described.

The first stopper section 9 is inserted into the inner circumference of the stopper frame 8 from the lower end opening (the opening on the side provided with the flange 16) of the stopper frame 8. The first stopper section 9 is formed of a member having elasticity greater than that of the stopper frame 8 and is deformed and contracted to be fitted between the retaining portions 18a and 18b provided in the inner circumference of the stopper frame 8. Alternatively, the first closed film 9a side of the first stopper section 9 is inserted from the stopper section fitting portion 13 as the upper end opening of the stopper frame 8 to be fitted between the retaining portions 18a and 18b.

The mounting hole 33 of the coupling segment 31 of the second stopper section 10 is fitted and fixed to the attachment part 24 of the stopper frame 8. The second stopper section 10 is formed of the same member having great elasticity as that of the first stopper section 9. The removal unit 27 is inserted into the stopper section fitting portion 13 of the stopper frame 8 by bending the coupling segment 31. When the removal unit 27 is deformed and contracted to be inserted into the stopper section fitting portion 13 of the stopper frame 8, the second seal 28 of the removal unit 27 is arranged in the inner circumference of the stopper frame 8 and is contacted in a water-tight manner with the periphery of the upper end opening of the first stopper section 9 fitted in the inner circumference of the stopper frame 8. The handle 30 is arranged to be overlapped with the upper surface of the tab 14 of the stopper frame 8. The second stopper section 10 is fitted between the notched grooves 15a and 15b provided in the stopper frame 8.

Fitting of the thus-assembled treatment instrument stopper 1 in the channel opening 6 of the treatment instrument insertion channel 7 of the endoscope 2 will be described. The assembled treatment instrument stopper 1 is previously sterilized. The sterilized treatment instrument stopper 1 is inserted from the lower end opening (the opening on the side provided with the flange 16) of the stopper frame 8 into the channel opening 6 of the treatment instrument insertion channel 7. The lower end opening of the stopper frame 8 passes over the flanged mouth provided in the channel opening 6 by the tilted surface 20 of the engagement portion 19. The mouth is fitted between the engagement portion 19 and the first seal 23 in the lower end opening of the first stopper section 9. The first seal 23 of the first stopper section 9 is contacted in a water-tight manner with the flanged mouth of the channel opening 6 (the state shown in FIG. 2). The channel opening 6 may be sealed to the stopper frame 8 without the first seal 23. In the state where the treatment instrument stopper 1 is fitted in the channel opening 6 of the treatment instrument insertion channel 7, the distal end of the treatment instrument 5, not shown, is inserted from the second treatment instrument insertion hole 25 provided in the second closed film 26 of the second stopper section 10 of the treatment instrument stopper 1 through the first treatment instrument insertion hole 11 provided in the first closed film 9a of the first stopper section 9 into the treatment instrument insertion channel 7.

For the insertion operation, the outer circumference of the treatment instrument 5 inserted into the treatment instrument stopper 1 is contacted with the second treatment instrument insertion hole 25 of the second stopper section 10 and the first treatment instrument insertion hole 11 of the first stopper section 9. The sealed state of the treatment instrument insertion channel 7 can be secured. If contaminants and air in a body cavity are flowed backward through the treatment instrument insertion channel 7, the first closed film 9a and the second closed film 26 can prevent them from being leaked out to the outside.

When the treatment instrument 5 having a very large outer diameter is used and the advance or retreat force amount of the insertion operation is large due to contact with the first closed film 9a and the second closed film 26, the second stopper section 10 is removed from the stopper frame 8 (the state shown in FIG. 3) and the treatment instrument 5 is inserted from the first treatment instrument insertion hole 11 of the first stopper section 9 into the treatment instrument insertion channel 7. The advance or retreat force amount of the insertion operation of the treatment instrument 5 having a large diameter is smaller. The sealed state of the treatment instrument insertion channel 7 can be secured.

When the second stopper section 10 is removed from the stopper frame 8, the handle 30 is held and pulled up to remove the removal unit 27 of the second stopper section 10 from the stopper section fitting portion 13 of the stopper frame 8. In removal of the second stopper section 10, the handle 30 of the second stopper section 10 is tilted at the angle α with respect to the tab 14 of the stopper frame 8, the operator can easily hold only the handle 30 and engages the finger onto the convex 29 provided in the handle 30 to easily pull up the handle 30. The second stopper section 10 removed from the stopper frame 8 is hung from the hinge 34 along, the outside of the stopper frame 8. The second stopper section 10 can be moved away from the position of a projected region Q of the stopper section fitting portion 13 of the stopper frame 8 and can be hung in the position not obstructing the insertion operation of the treatment instrument 5 into the stopper section fitting portion 13 of the stopper frame 8 and the first treatment instrument insertion hole 11 of the first stopper section 9.

The treatment instrument 5 of this embodiment is inserted through the projected region Q into the treatment instrument insertion channel 7 in the insertion operation. The coupling segment 31 (more correctly, the hinge 34) functions to be moved away from the projected region Q as an example of the insertion range. When the second stopper section 10 is removed from the stopper section fitting portion 13, the second stopper section 10 can be prevented from obstructing the insertion operation of the treatment instrument 5.

The operation removing the treatment instrument stopper 1 from the channel opening 6 of the treatment instrument insertion channel 7 will be described using FIG. 6 together. When the treatment instrument stopper 1 is removed from the channel opening 6, only the tab 14 of the stopper frame 8 is held or the tab 14 of the stopper frame 8 and the handle 30 of the second stopper section 10 are held together. The held tab 14 is pulled up in the direction of the index 17 or in the arrow direction in FIG. 6. The tab 14 is pulled up to tear the notched grooves 15a and 15b provided in the stopper frame 8, and then, the stopper frame 8 is torn from the upper surface to the side surface of the stopper frame 8. The stopper frame 8 is torn from the notched grooves 15a and 15b to be easily removed from the channel opening 6. The removed treatment instrument stopper 1 cannot be reused by the torn stopper frame.

In this embodiment, in the state where the second stopper section 10 is fitted, the second stopper section 10 is held to the stopper frame 8 in two points of the attachment part 24 and the removal unit 27. Such being held in two points will be called "held at both ends." Here, as apparent from FIG. 2, the term "both ends" means that the second stopper section 10 is held at both ends and also means a state in general that the second stopper section 10 is held in two points. The state where the second stopper section 10 is held at both ends so that the tearing (in the example of this embodiment, the notched grooves 15a and 15b forming the tearing) is not positioned in a region between the portions provided for holding the second stopper section 10 (in the example of this embodiment, the attachment part 24 and the removal unit 27) will be called "held at both ends without passing over the tearing." In such state where is, when the second stopper section 10 is fitted in the stopper section fitting portion, the second stopper section 10 is "held at both ends without passing over the tearing." When the tab 14 is pulled up to collapse the stopper frame 8, the second stopper section 10 cannot obstruct tearing in the tearing (the notched groove 15b) and the stopper frame 8 can be easily removed from the channel opening 6.

In removal of the treatment instrument stopper 1, regardless of the fitted state of the second stopper section 10 to the stopper frame 8, the pullup operation of the tab 14 can easily and reliably tear the stopper frame 8 so that the treatment instrument stopper 1 cannot be reliably reused.

In tearing and removal of the stopper frame 8, the lower end of the stopper frame 8 is provided with the flange 16. The proximal end of the stopper frame 8 is stable and the tearing operation from the notched grooves 15a and 15b can be reliably executed. When the treatment instrument 5 is inserted through the first stopper section 9 and the second stopper section 10, the flange 16 can prevent falling of the treatment instrument 5 to the outside by stabling the base of the stopper frame 8. The contact between the first treatment instrument insertion hole 11 of the first stopper section 9, the second treatment instrument insertion hole 25 of the second stopper section 10, and the treatment instrument 5 can be held. The contact between the mouth of the channel opening 6 of the treatment instrument insertion channel 7 and the first seal 23 of the first stopper section 9 can be also held. As shown in FIG. 1, a height H between the lower surface of the first treatment instrument insertion hole 11 of the first stopper section 9 and the upper surface of the second treatment instrument insertion hole 25 of the second stopper section 10 is formed to be larger than an inner diameter D of the channel opening 6 (H≧D). The fall angle of the inserted treatment instrument 5 can be small and the treatment instrument 5 can be stably inserted and held.

The first stopper section 9 and the second stopper section 10 can be assembled into the stopper frame 8 by simple pressing. Automatic assembling by machining is possible. The efficiency of the assembling operation is improved. The sterilizing process and packaging after the sterilizing process can be both automated.

The endoscope treatment instrument stopper of this embodiment has a construction in which the stopper frame 8 and the second stopper section 10 are formed independently. Materials suitable for the stopper frame 8 and the second stopper section 10 are used to form the endoscope treatment instrument stopper. The degree of freedom of the material selection is improved. The position of the removal unit 27 is frequently changed with removal from the attachment part 24. The material forming the second stopper section 10 preferably has high flexibility. The stopper frame 8 can be contacted with and fixed to the channel opening 7 and is preferably torn reliably when removed from the channel opening 7. The stopper frame 8 is preferably formed of a material having no flexibility. The material suitable for the second stopper section 10 is different from the material suitable for the stopper frame 8. In this embodiment, a construction in which the stopper frame 8 and the second stopper section 10 are formed independently is employed. The materials suitable for them can be used. A characteristic more excellent than the integrally formed treatment instrument stopper can be realized.

Figure 10:
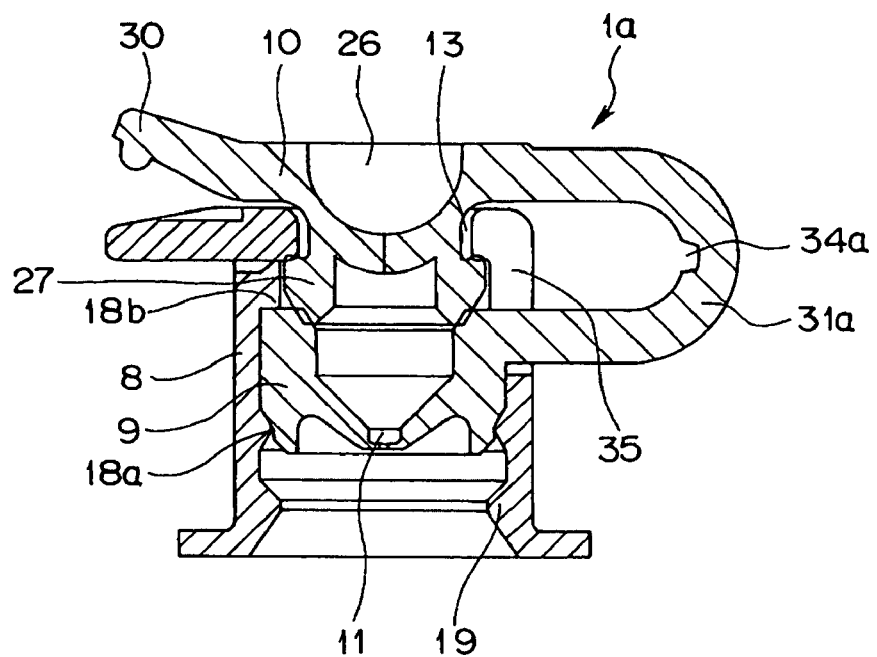
FIG. 10 is a cross-sectional view showing the construction of a second embodiment of an endoscope treatment instrument stopper according to the present invention.

A second embodiment of the treatment instrument stopper according to the present invention will be described using FIG. 10. The same portions as those of FIGS. 1 to 9 are represented by like reference numerals and the detailed description is omitted.

A treatment instrument stopper 1*a* of the second embodiment has the first stopper section 9 formed integrally with the second stopper section 10. In place of the coupling segment 31 of the second stopper section 10, the treatment instrument stopper 1*a* is provided with a coupling segment 31*a* extended from the second stopper section 10 to be coupled to the outside upper surface of the first stopper section 9. The middle portion of the coupling segment 31*a* is provided with a hinge 34*a* for easily folding the coupling segment 31*a*. The outside of the stopper frame 8 is provided with a coupling segment insertion groove 35 into which the coupling segment 31*a* coupling the first stopper section 9 and the second stopper section 10 is inserted.

In such construction, the first stopper section 9 is inserted from the stopper section fitting portion 13 on the upper surface of the stopper frame 8 to be fitted between the retaining portions 18*a* and 18*b*. The coupling segment 31*a* extended from the first stopper section 9 is inserted into the coupling segment insertion groove 35 of the stopper frame 8. The removal unit 27 of the second stopper section 10 is fitted in the stopper section fitting portion 13 of the stopper frame 8. Fitting of the treatment instrument stopper 1*a* in the channel opening 6 of the treatment instrument insertion channel 7 and removal of the treatment instrument stopper 1*a* from the channel opening 6 can be executed in the same method as that of the first embodiment.

The treatment instrument stopper 1*a* of the second embodiment has the same effect as that of the first embodiment. The first stopper section 9 is formed integrally with the second stopper section 10. The component construction is simple and the cost can be reduced.

A third embodiment of the treatment instrument stopper according to the present invention will be described using FIG. 11. The same portions as those of FIGS. 1 to 9 are represented by like reference numerals and the detailed description is omitted.

A treatment instrument stopper 1*b* of the third embodiment is different from the first embodiment in that the position of the attachment part 24 attaching the coupling segment 31 of the second stopper section 10 is different. In the first embodiment, the attachment part 24 is provided in the position in which the coupling segment 31 of the second stopper section 10 is fixed in parallel between the notched grooves 15*a* and 15*b* provided in the stopper frame 8.

In the third embodiment, an attachment part 24' is provided in the position in which the coupling segment 31 of the second stopper section 10 is orthogonal to the notched grooves 15*a* and 15*b* provided in the stopper frame 8. The second stopper section 10 fitted in the stopper section fitting portion 13 of the stopper frame 8 crosses over the notched grooves 15*a* and 15*b*.

In the state where the second stopper section 10 is fitted in this manner, when the tab 14 of the stopper frame 8 is held to tear the stopper frame 8 from the notched grooves 15*a* and 15*b*, the tab 14 of the stopper frame 8 is brought into contact with the second stopper section 10 to prevent the stopper frame 8 from being torn from the notched grooves 15*a* and 15*b*. Unless the second stopper section 10 is removed from the stopper section fitting portion 13 of the stopper frame 8, the stopper frame 8 cannot be torn from the notched grooves 15*a* and 15*b*. It is thus possible to prevent tearing the stopper frame 8 by pulling up the tab 14 by mistake.

Figure 11:
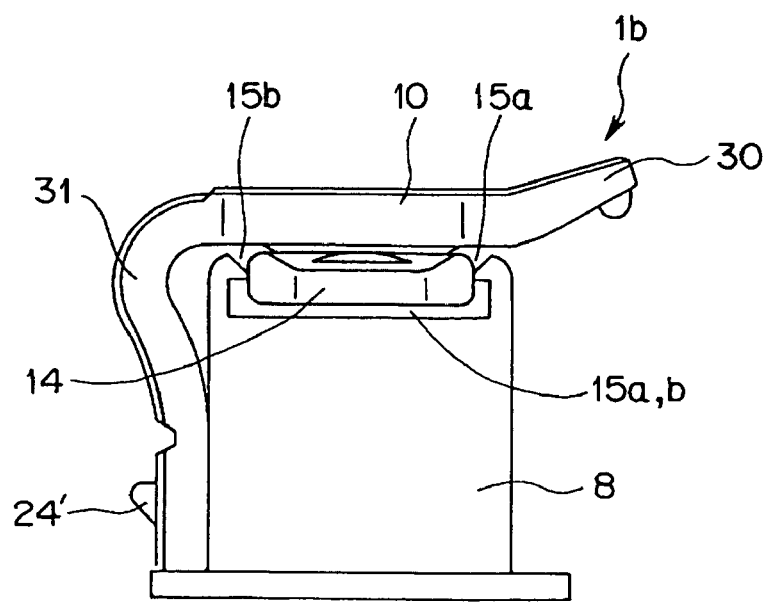
FIG. 11 is a side view showing the construction of a third embodiment of an endoscope treatment instrument stopper according to the present invention.

In this embodiment, in the state where the second stopper section 10 is fitted, the second stopper section 10 is held to the stopper frame 8 in two points of the attachment part 24' and the removal unit 27 (not shown in FIG. 11). Such being held in two points will be called "held at both ends." As apparent from the construction of FIG. 11, the term "both ends" means that the second stopper section 10 is held at both ends and also means a state in general that the second stopper section 10 is held in two points. The state where the second stopper section 10 is held at both ends so that the tearing (in the example of this embodiment, the notched groove 15*b* forming the tearing) is positioned in a region between the portions provided for holding the second stopper section 10 (in the example of this embodiment, the attachment part 24' and the removal unit 27) will be called "held at both ends by passing over the tearing." In such state where is, when the second stopper section 10 is fitted in the stopper section fitting portion, the second stopper section 10 is "held at both ends by passing over the tearing." When the tab 14 is pulled up to collapse the stopper frame 8, tearing is stopped since the second stopper section 10 is positioned above the tearing (the notched groove 15*b*) and erroneous collapse when the tab 14 is pulled up by mistake can be prevented.

Figure 12:
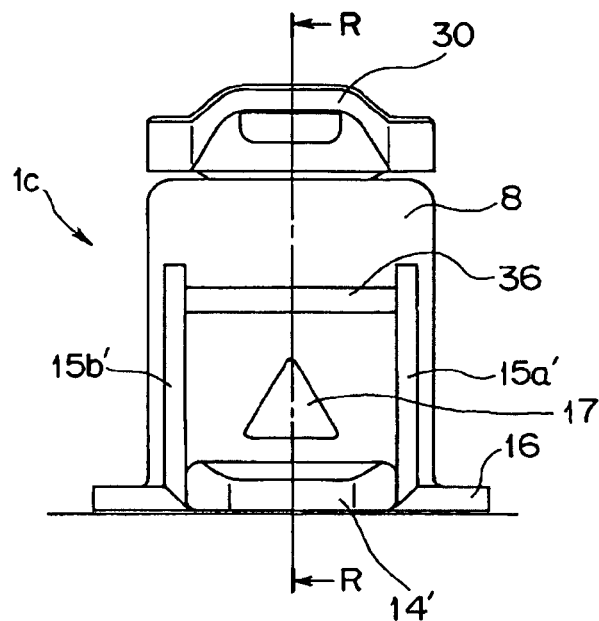
FIG. 12 is a side view showing the construction of a fourth embodiment of an endoscope treatment instrument stopper according to the present invention.
Figure 13:
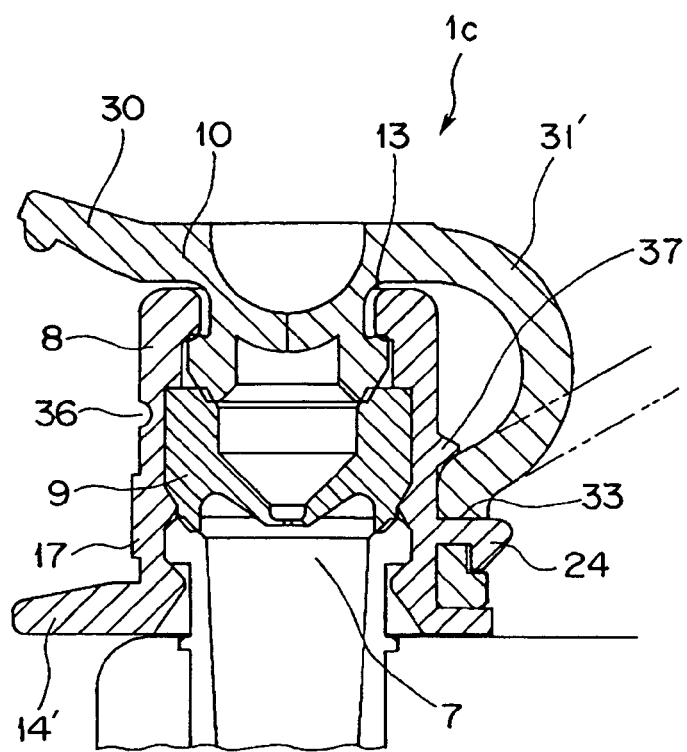
FIG. 13 is a cross-sectional view showing the construction of the fourth embodiment of the endoscope treatment instrument stopper according to the present invention, taken along cut line R-R of FIG. 12.

A fourth embodiment of the treatment instrument stopper according to the present invention will be described using FIGS. 12 and 13. FIG. 12 is a side view showing the construction of the fourth embodiment of the endoscope treatment instrument stopper according to the present invention; FIG. 13 is a cross-sectional view showing the fourth embodiment of the endoscope treatment instrument stopper according to the present invention, taken along cut line R-R of FIG. 12. The same portions as those of FIGS. 1 to 9 are indicated by like reference numerals and the detailed description is omitted.

The fourth embodiment is different from the first embodiment in that the positions of the tab 14 and the notched grooves 15*a* and 15*b* provided in the stopper frame 8 are different. A treatment instrument stopper 1*c* of the fourth embodiment forms a tab 14' by cutting away a part of the flange 16 provided in the outer circumference on the lower end side of the stopper frame 8. Notched grooves 15*a'* and 15*b'* are formed on the side surface of the stopper frame 8 from both sides of the tab 14'. The upper end side of the notched grooves 15*a'* and 15*b'* are extended in the upper direction to portions above the substantially half portion of the upper and lower directions in the drawing of the stopper frame 8 and are provided with a folding portion 36 formed by a notched groove coupling the upper ends of the notched grooves 15a' and 15b'.

The tab 14' formed in a part of the flange 16 is pulled up to tear the notched grooves 15a' and 15b' and the outside of the stopper frame 8 is then torn to the folding portion 36. The stopper frame 8 can be easily removed from the channel opening 6. The index 17 indicating the pullup direction of the tab 14' is formed between the notched grooves 15a' and 15b' provided on the side surface of the stopper frame 8. The pullup direction of the tab 14' can be easily recognized.

A coupling segment 31' of the second stopper section 10 of the treatment instrument stopper 1c of the fourth embodiment does not have the hinge 34 provided on the coupling segment 31 of the second stopper section 10 of the treatment instrument stopper 1 of the first embodiment. Instead, the outside of the stopper frame 8 to which the coupling segment 31' of the second stopper section 10 is attached is provided with a bend restriction portion 37. The bend restriction portion 37 is formed to be in a convex shape protruded outward in the upper position in the drawing of the attachment part 24 to which the mounting hole 33 at the edge of the coupling segment 31' of the second stopper section 10 is fixed. The mounting hole 33 of the coupling segment 31' is fixed to the attachment part 24 of the stopper frame 8 and is held between the attachment part 24 and the bend restriction portion 37. When the second stopper section 10 is removed from the stopper section fitting portion 13 of the stopper frame 8, as indicated by the phantom lines in the drawing, the coupling segment 31' can be left to be tilted substantially diagonally to the stopper frame 8. The same effect as that of the first embodiment can be obtained. The removed second stopper section 10 can be moved away from the position obstructing the insertion operation of the treatment instrument 5.

Figure 14:
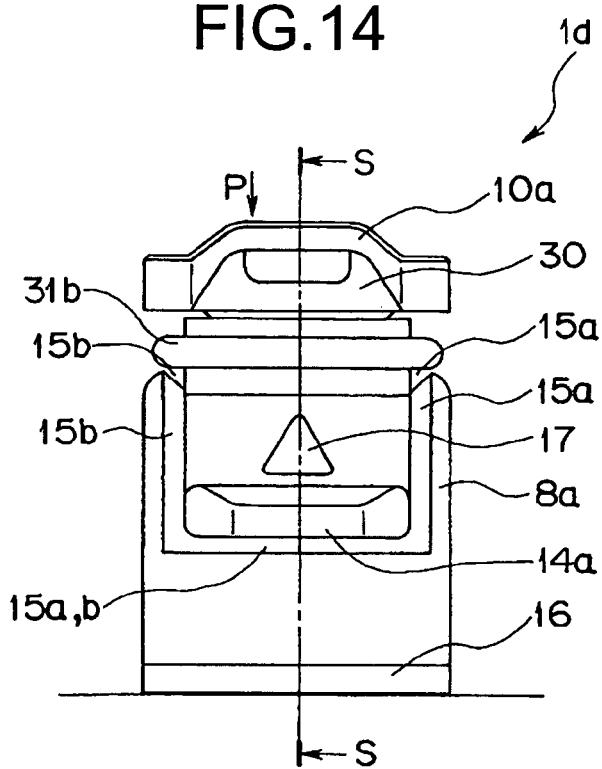
FIG. 14 is a side view showing the construction of a fifth embodiment of an endoscope treatment instrument stopper according to the present invention.
Figure 15:
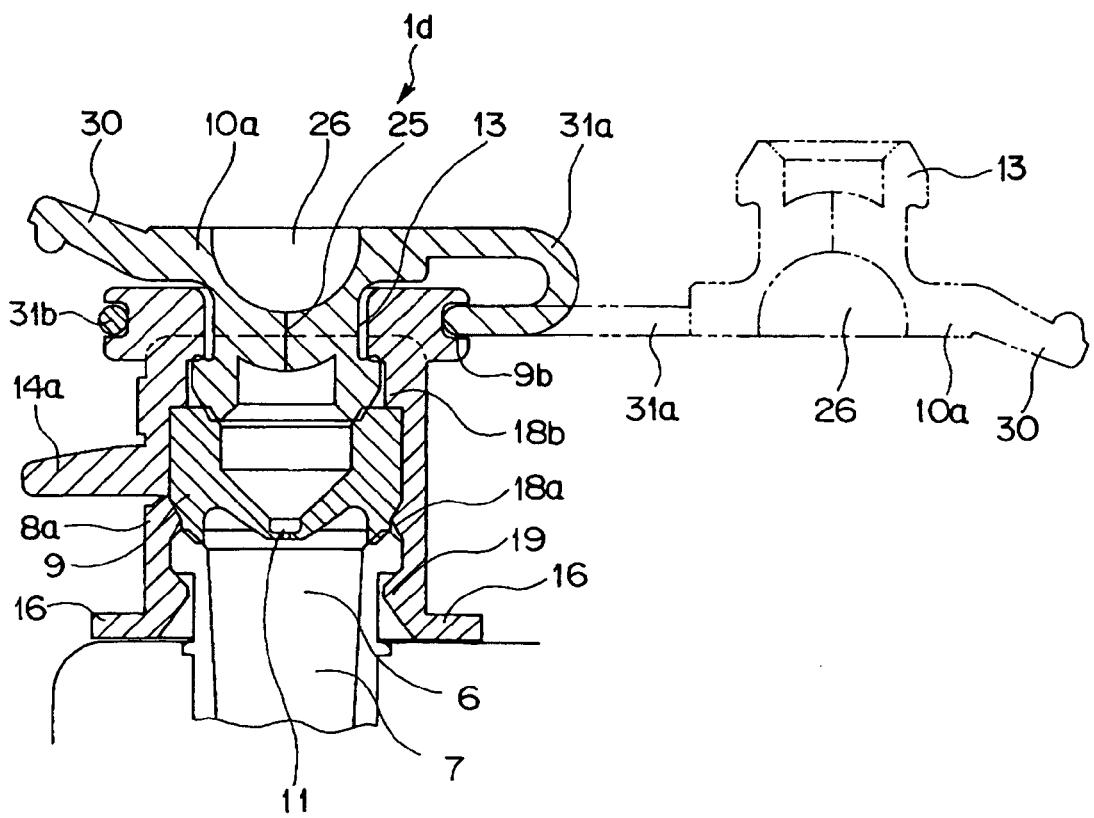
FIG. 15 is a cross-sectional view showing the construction of the fifth embodiment of the endoscope treatment instrument stopper according to the present invention, taken along cut line S-S of FIG. 14.
Figure 16:
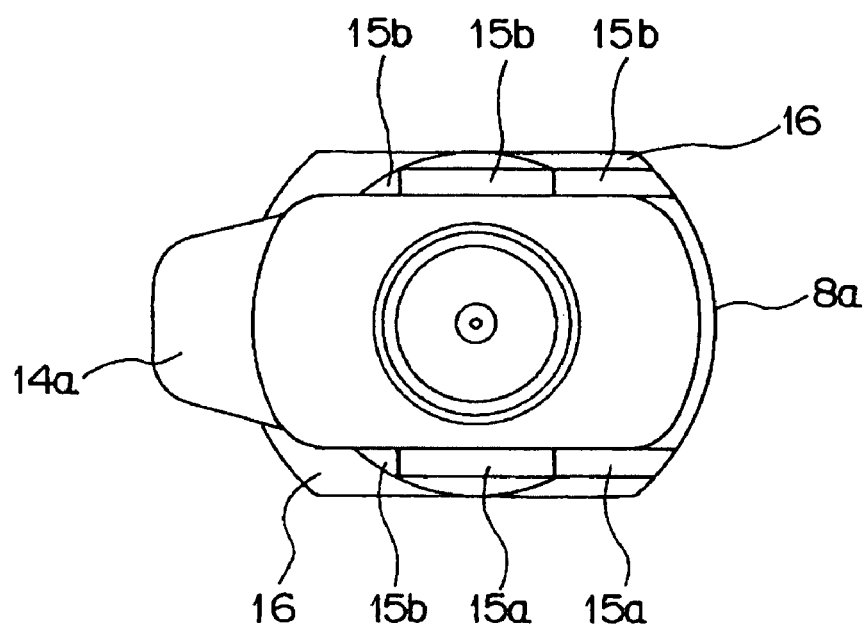
FIG. 16 is a top view of a stopper frame seen in the direction of arrow P of FIG. 14 in the fifth embodiment of the endoscope treatment instrument stopper according to the present invention.
Figure 17:
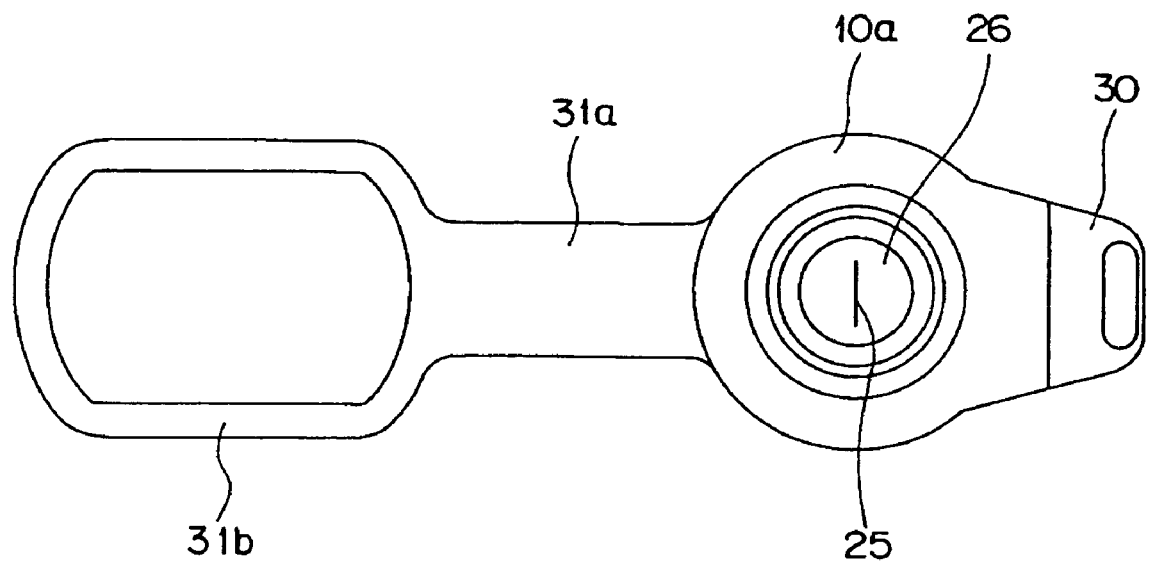
FIG. 17 is a plan view showing the construction of a second stopper section of the fifth embodiment of the endoscope treatment instrument stopper according to the present invention.
Figure 18:
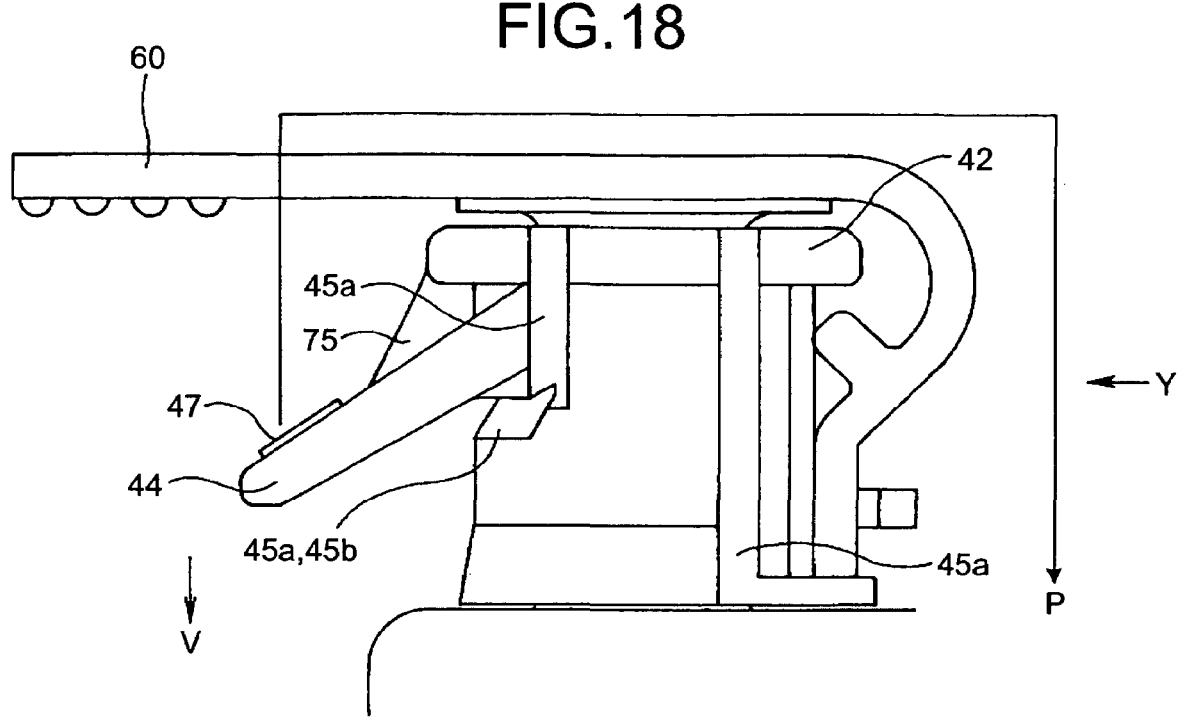
FIG. 18 is a side view of a treatment instrument stopper of a sixth embodiment of an endoscope treatment instrument stopper according to the present invention.

A fifth embodiment of the treatment instrument stopper according to the present invention will be described using FIGS. 14 to 17. FIG. 14 is a side view showing the construction of the fifth embodiment of the endoscope treatment instrument stopper according to the present invention; FIG. 15 is a cross-sectional view showing the construction of the fifth embodiment of the endoscope treatment instrument stopper according to the present invention; FIG. 16 is a top view of a stopper frame 8a of the fifth embodiment of the endoscope treatment instrument stopper according to the present invention, seen in the direction of arrow P of FIG. 14; FIG. 17 is a plan view showing the construction of a second stopper section of the fifth embodiment of the endoscope treatment instrument stopper according to the present invention. The same portions as those of FIGS. 1 to 9 are represented by like reference numerals and the detailed description is omitted.

A treatment instrument stopper 1d used for the endoscope of the fifth embodiment has a construction different from that of the stopper frame 8 and the second stopper section 10 of the treatment instrument stopper 1 of the first embodiment. In the stopper frame 8a of the treatment instrument stopper 1d, as shown in FIGS. 14 and 15, a tab 14a is extended outward from the substantially middle portion on the outside of the stopper frame 8a. The tab 14a is formed to have a geometry substantially equal to that of the tab 14a. The notched grooves 15a and 15b are provided on the outside of the stopper frame 8 from the base portion of the tab 14a. When the tab 14a is lifted in the upper direction in the drawing, the notched grooves 15a and 15b tear the stopper frame 8a. The notched grooves 15a and 15b are extended from the outside provided with the tab 14a of the stopper frame 8a via the outside opposite the upper surface and the tab 14a to the flange 16.

When the stopper frame 8a fitted in the channel opening 6 is removed, the tab 14a is held to be turned in the upper direction in the drawing to tear the stopper frame 8a from the notched grooves 15 and 15b. The stopper frame 8a can be easily removed from the channel opening 6 so that the treatment instrument stopper 1d cannot be reused.

The outer circumference of the upper portion of the stopper frame 8a is provided with a fitting groove 9b in which a ring 31b of a later-described second stopper section 10a is fitted. The fitting groove 9b, as shown in FIG. 17, is fitted with the ring 31b in a substantially rectangular shape provided at the edge of the coupling segment 31a extended from the side opposite the handle 30 of the second stopper section 10a. The fitting groove 9b of the stopper frame 8a is formed to have the same shape as that of the ring 31b. The shape of the ring 31b and the fitting groove 9b may be an atypical shape having a parallel unit other than the substantially rectangular shape. Positioning is easy when the ring 31b of the second stopper section 10a is fitted in the fitting groove 9b of the stopper frame 8a. Fitting and removal of the second stopper section 10a in/from the stopper section fitting portion 13 of the stopper frame 8a are easy.

When the second stopper section 10a is removed from the stopper section fitting portion 13 of the stopper frame 8a by the holding operation of the handle 30, as indicated by the phantom lines in FIG. 15, it can be arranged in the position away from the projection opening position of the stopper section fitting portion 13.

The same effect as that of the first embodiment can be obtained. The removed second stopper section 10a can be moved away from the position obstructing the insertion operation of the treatment instrument 5.

The endoscope treatment instrument stopper according to a sixth embodiment will be described using FIGS. 18 to 24. A treatment instrument stopper 1e has a stopper frame 38 formed of a plastic material such as polyethylene having slight elasticity, a first stopper section 39 formed of a material such as silicon rubber having elasticity greater than that of the stopper frame 38, and a second stopper section 40 formed of a material such as silicon rubber.

The stopper frame 38 is formed in a substantially cylindrical shape having an upper end wall 42 and has a tab 44 extended diagonally downward and formed integrally with a part of the outer circumference surface of the upper end wall 42 and the stopper frame 38. The upper end wall 42 is provided with a flange substantially circumferentially thereof and is provided with a stopper section fitting portion 43 from which the later-described second stopper section 40 is removed.

Protruded retaining portions 48a and 48b for fitting and retaining the outer circumference of the later-described first stopper section 39 are circumferentially or partially formed on the inner circumference surface in the substantially cylindrical middle portion of the stopper frame 38. A protruded engagement portion 49 for fitting the stopper frame 38 in the channel opening 6 of the treatment instrument insertion channel 7 of the endoscope 2 is circumferentially or partially formed on the inner circumference surface at the lower end of the stopper frame 38. The protruded engagement portion 49 has the tilted surface 20 on the opening side at the lower end of the stopper frame 38. The engagement portion 49 can easily press fit the stopper frame 38 to the outer circumference of the channel opening 6 by the tilted surface 20. When the stopper frame 38 is pressed into the channel opening 6, the engagement portion 49 is formed to easily engage the stopper frame 38 with the channel opening 6 beyond a flanged mouth thereof by the tilted surface 20. When the engagement portion 49 is once engaged, the stopper frame 38 cannot be easily removed from the channel opening 6. As described later, unless the stopper section 38 is collapsed, the treatment instrument stopper 1e cannot be removed from the channel opening 6. The shape of the engagement portion 49 and the mouth shape of the channel opening 6 are not limited to those of this embodiment. Any shape in which the stopper frame 38 can be easily fitted in the channel opening 6 and the fitted stopper frame 38 cannot be removed from the channel opening 6 may be used.

Figure 19:
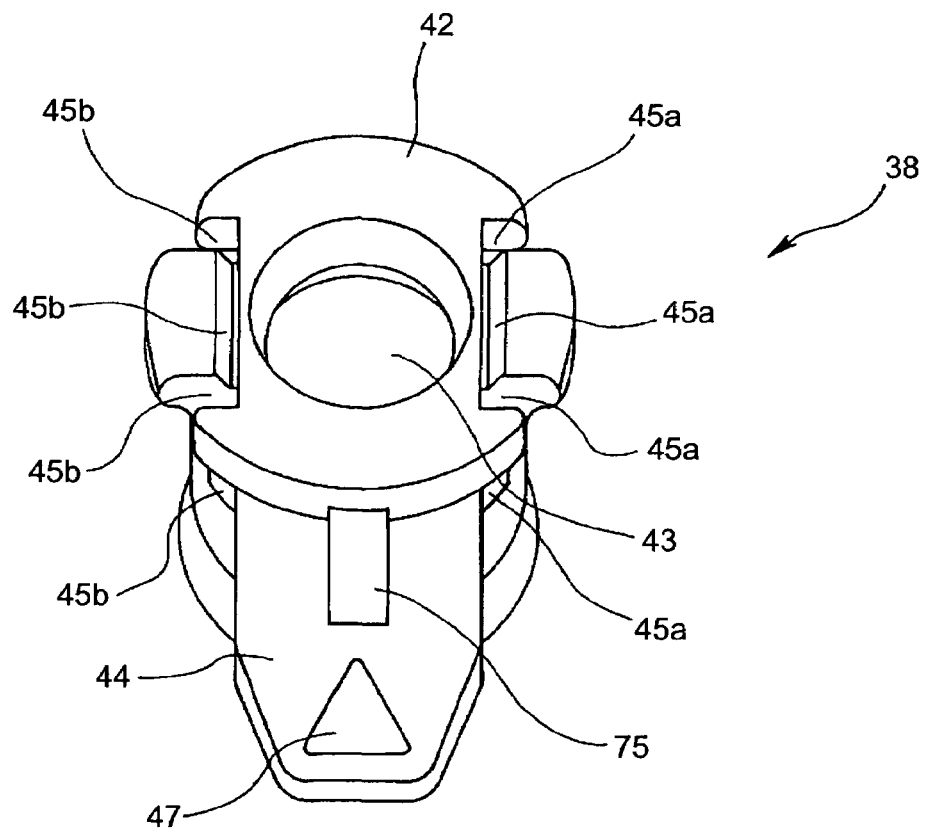
FIG. 19 is a view of the appearance of a stopper frame alone of the treatment instrument stopper according to the sixth embodiment of the endoscope treatment instrument stopper according to the present invention, seen from the diagonally upper side.
Figure 20:
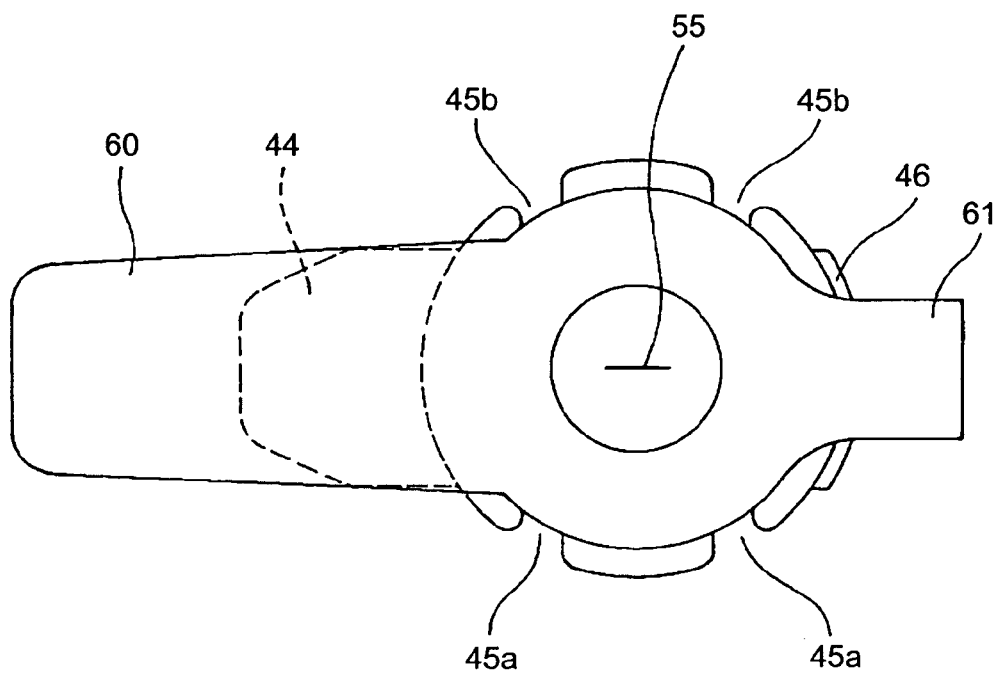
FIG. 20 is a top view of a stopper section of the treatment instrument stopper according to the sixth embodiment of the endoscope treatment instrument stopper according to the present invention, fitted in the stopper frame.
Figure 21:
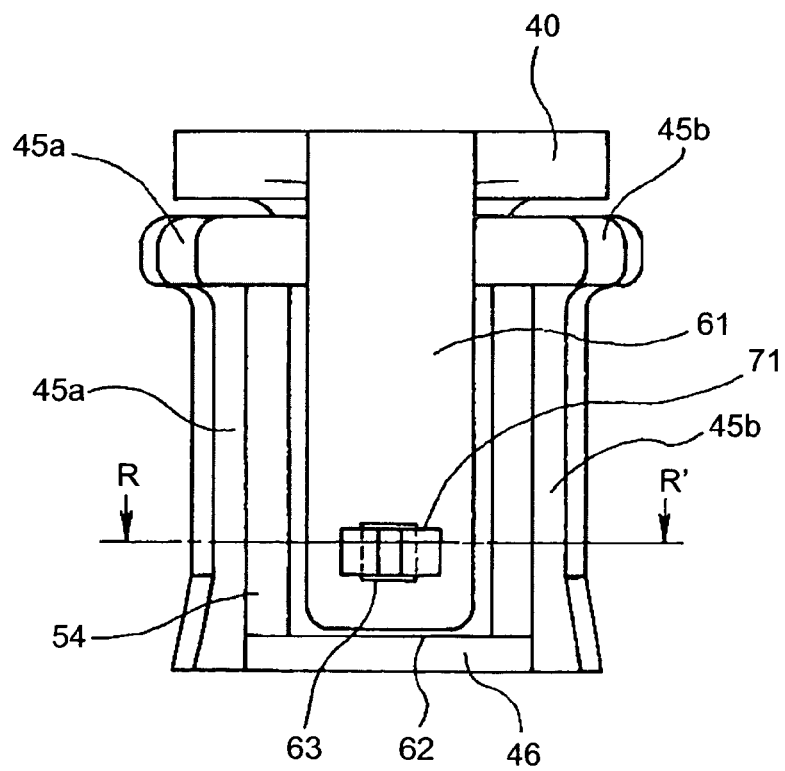
FIG. 21 is a rear view of the treatment instrument stopper according to the sixth embodiment of the endoscope treatment instrument stopper according to the present invention, seen in the direction of arrow Y shown in FIG. 18.

The upper end wall 42, as shown in FIG. 19, is provided with a tearing including a pair of notched grooves 45a and 45b. One end of each of the notched grooves 45a and 45b as the tearing is formed at a pitch substantially equal to the width of the tab 44 and is connected to the base on the back side of the tab 44.

The other end of each of the pair of notched grooves 45a and 45b is extended to the upper end wall 42, the side surface of the stopper frame 38, and a flange 46 from the upper side to the lower side of the stopper frame 38 opposite the side provided with the tab 44. When the tab 44 is pulled up to remove the stopper frame 38 from the channel opening 6, the pair of notched grooves 45a and 45b are formed to easily tear the stopper frame 38 therefrom. An attachment part 54 having an arrow-shaped portion for fitting and holding the second stopper section 40 is formed between the pair of notched grooves 45a and 45b provided in the outer circumference portion of the stopper frame 38. The pair of notched grooves 45a and 45b are provided on the side surface of the stopper frame 38 and are thinner than other portions of the stopper frame 38.

The pair of notched grooves 45a and 45b formed to be easily torn by the tab 44 need not be notched grooves leaving the thin wall unlike this embodiment and may be openings connected to the inner circumference surface to be torn by a smaller force. The surface of the tab 44 is provided with an index 47 easily indicating the general operation direction of the tab 44. The collapse direction side of the tab 44 is provided with a rib 75.

The first stopper section 39 has a cylindrical outer shape and is provided at the upper end in the inner circumference with a first closed film 39a formed in a substantially funnel shape. The center portion of the first closed film 39a is provided with a first treatment instrument insertion hole 41. The first treatment instrument insertion hole 41 is provided with a small hole 51. When the treatment instrument 5 is inserted into the first treatment instrument insertion hole 41, the small hole 51 is deformed and extended according to the size of the outer diameter of the treatment instrument 5.

The first stopper section 39 is formed by a geometry equal to the size of the inner diameter of the stopper frame 38 or slightly smaller than the size of the inner diameter of the stopper frame 38 so that the outer circumference surface of the first stopper section 39 is fitted and retained between the retaining portions 48a and 48b provided on the inner circumference surface in the middle portion of the stopper frame 38. When the first stopper section 39 is inserted from the lower end opening of the stopper frame 38 to be brought into contact with the retaining portion 48b beyond the engagement portion 49 and the retaining portion 48a provided on the inner circumference surface of the stopper frame 38 and is fitted between the retaining portions 48a and 48b. The assembling operation inserting and fitting the first stopper section 39 into the stopper frame 38 is a simple one-way pressing operation and can easily realize automatic assembling by machining. The lower end of the first stopper section 39 is provided with a first seal 53a contacting in an air-tight manner the first stopper section 39 with the circumference of the mouth of the channel opening 6 when the stopper frame 38 is fitted in the channel opening 6. The first treatment instrument insertion hole 41 provided in the first closed film 39a of the first stopper section 39 in a shape in which the first closed film 39a is contacted with the outer circumference of the inserted treatment instrument 5 need not be a small hole and may be a slit.

The second stopper section 40 is fitted in the stopper section fitting portion 43 provided on the upper end wall 42 of the stopper frame 38. The second stopper section 40 has a removal unit 57 in a substantially cylindrical shape, a handle 60 extended from the upper surface side of the removal unit 57, and a coupling segment 61 opposite the handle 60 to be extended from the upper surface side of the removal unit 57, which are integrally formed.

The upper opening of the removal unit 57 of the second stopper section 40 is provided with a hemispherical second closed film 56 having the function of guiding insertion of the treatment instrument 5. The center of the second closed film 56 is provided with a second treatment instrument insertion hole 55 formed in a slit communicated with the upper and lower sides of the second closed film 56 and has a forming direction of a slit hole in which its longitudinal direction is substantially equal to the direction removing the second stopper section 40 from the stopper section fitting portion 43 provided on the stopper frame 38. The second treatment instrument insertion hole 55 in a shape in which the second treatment instrument insertion hole 55 is contacted with the outer circumference of the inserted treatment instrument 5 need not be a slit and may be a small hole.

The lower opening end of the removal unit 57 of the second stopper section 40 is provided with a second seal 58 contacted in an air-tight manner with the circumference of the upper opening of the first stopper section 39 when the removal unit 57 is fitted in the stopper section fitting portion 43 provided in the stopper frame 38.

Figure 22:
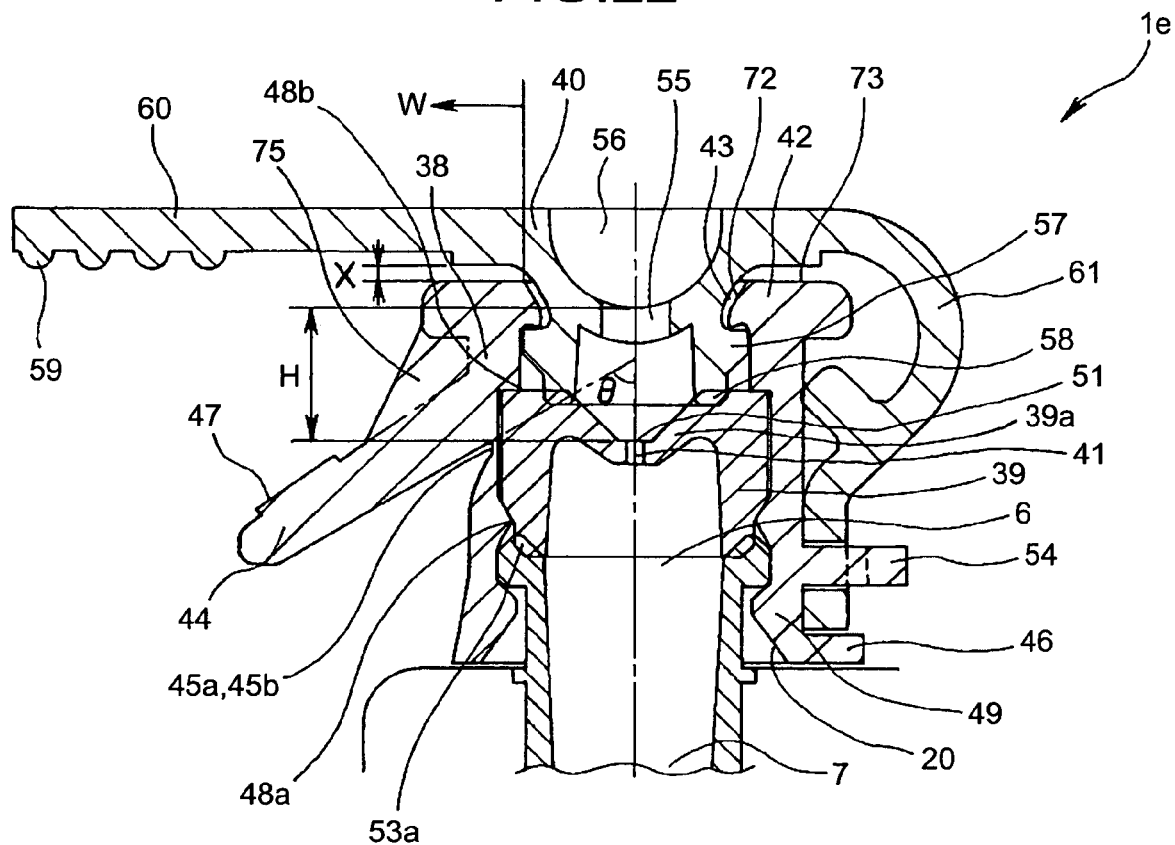
FIG. 22 is a cross-sectional view showing the state where the treatment instrument stopper according to the sixth embodiment of the endoscope treatment instrument stopper according to the present invention is fitted in the opening unit of the treatment instrument insertion channel provided in the endoscope body.
Figure 23:
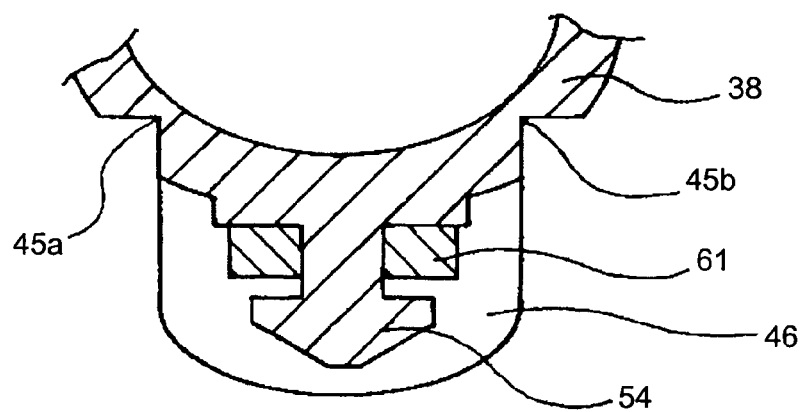
FIG. 23 is a view of the treatment instrument stopper according to the sixth embodiment of the endoscope treatment instrument stopper according to the present invention in which a part of the cross section taken along line R-R' shown in FIG. 21 is seen from top.

The handle 60 provided in the second stopper section 40 is formed to be extended in the outside direction of the second closed film 56 on the extension line in the forming direction of the slit hole of the stopper section fitting portion 43, that is, in the direction indicated by W in FIG. 22. In this case, the handle 60 is provided in the position upper than the tab 44, that is, in the position in which the distance from the channel opening 6 to the handle 60 is longer than that from the channel opening 6 to the tab 44 in the state where the stopper frame 38 is fitted in the channel opening 6 and the second stopper section 40 is fitted in the stopper section fitting portion 43. When the removal unit 57 of the second stopper section 40 is fitted in the stopper frame 38, the handle 60 is provided in the position away from the upper side of the tab 44 provided in the stopper frame 38 by the pitch of a distance X as indicated in FIG. 22 so as to cover the tab 44.

The handle 60 is formed to have a holding length longer than that of the tab 44 and a held area larger than that of the tab 44 and is provided with a plurality of convexes 59 on the surface opposite the tab 44. The pitch between the handle 60 and the tab 44 is formed so that the extension direction of the tab 44 is at an acute angle with respect to the center axis of the channel opening 6 (θ<90° shown in FIG. 22) and that the top end of the tab 44 is extended toward the channel opening 6 side. The pitch between the handle 60 and the tab 44 on the distal end of the handle 60 is larger than that on the proximal end of the handle 60. The handle 60 is formed of a material such as silicon rubber and is softer than the tab 44 formed of a material such as polyethylene.

The force amount when the tab 44 is held to stress the notched grooves 45a and 45b, and the stopper frame 38 is collapsed to be removed from the channel opening 6, that is, the collapse start force amount of the stopper frame 38, is larger than the removal force amount when the handle 60 is held to perform the pullup operation and the second stopper section 40 is removed from the stopper section fitting portion 43.

The handle 60 and the tab 44 are different in construction including the difference in the shape and the quality of material, the position relation, and the magnitude relation of the fold force amount. When the operator holds the handle 60 to remove the removal unit 57 and advances various treatments by the changing from the second treatment instrument insertion hole 55 to the first treatment instrument insertion hole 41, the changing from the second treatment instrument insertion hole 55 to the first treatment instrument insertion hole 41 can be easily done without collapsing the stopper frame 38 due to erroneous operation of the tab 44.

The coupling segment 61 of the second stopper section 40 is formed on the opposite side of the handle 60 in a belt shape extended from the upper surface side of the removal unit 57 and is arranged in parallel between the pair of the notched grooves 45a and 45b of the stopper frame 38. In the state where the second stopper section 40 is fitted in the stopper section fitting portion 43 of the stopper frame 38, the coupling segment 61 is provided to be interposed between the notched grooves 45a and 45b of the stopper frame 38. The second stopper section 40 partially covers the notched grooves 45a and 45b and cannot cross over the notched grooves 45a and 45b. The end of the coupling segment 61 is provided with a mounting hole 63 into which the attachment part 54 having an arrow-shaped portion provided on the side surface of the stopper frame 38 is inserted. The mounting hole 63 of the coupling segment 61 of the second stopper section 40 can be fitted in the attachment part 54 of the stopper frame 38. The assembling operation inserting and fitting the mounting hole 63 of the second stopper section 40 into the attachment part 54 of the stopper frame 38 is a simple one-way pressing operation. Automatic assembling by machining can improve the efficiency of the operation.

A support portion 70 is formed to be protruded near the position provided with the mounting hole 63 of the coupling segment 61 at the stopper frame 38 side of the coupling segment 61. When the second stopper section 40 is removed from the stopper section fitting portion 43 to be released, it is hung in the position in which a part thereof is moved away from the treatment instrument insertion range Q of the stopper section fitting portion 43 of the stopper frame 38. The end surface of the coupling segment 61 is provided with a planar portion 62. The planar portion 62 is brought into contact with or close to the flange 46 of the stopper frame 38.

The second stopper section 40 in the state where the coupling segment 61 is attached to the attachment part 54 of the stopper frame 38 contacts in an air-tight manner the periphery of the upper opening of the first stopper section 39 held to the inner circumference of the stopper frame 38 with the second seal 58 of the second stopper section 40 when the removal unit 57 is inserted into the stopper section fitting portion 43 of the stopper frame 38.

To remove the removal unit 57 of the second stopper section 40 from the stopper section fitting portion 43 of the stopper frame 38, the handle 60 may be just held and pulled up. The removed second stopper section 40 is hung along the outside of the stopper frame 38 by the support portion 70. The coupling segment 61 can be prevented from being rotated and fallen by the planer unit 62 provided at its end.

In the state where the removal unit 57 of the second stopper section 40 is fitted in the stopper section fitting portion 43 of the stopper frame 38, an inner surface 72 and an upper surface 73 of the stopper section fitting portion 43, that is, the surfaces of a portion in which the second stopper section 40 of the stopper frame 38 is fitted, are substantially covered by the second stopper section 40 formed of an elastic body. The distance H from the second treatment instrument insertion hole 55 to the first treatment instrument insertion hole 41 is set to 9 mm or less. In consideration of the thickness of the second treatment instrument insertion hole 55, the distance H between the upper surface of the opening of the second treatment instrument insertion hole 55 and the upper surface of the opening of the first treatment instrument insertion hole 41 is 9 mm or less. In the state where the second stopper section 40 is removed from the stopper section fitting portion 43 of the stopper frame 38, the end surface of the stopper section fitting portion 43 of the stopper frame 38, that is, the distance h from the upper surface 73 to the first treatment instrument insertion hole 41, is set to 9 mm or less. The distance h between the center portion of the stopper section fitting portion 43 and the upper surface of the opening of the first treatment instrument insertion hole 41 which are in the same plane as that of the upper surface 73 is 9 mm or less.

Assembling of the treatment instrument stopper 1e including the stopper frame 38, the first stopper section 39, and the second stopper section 40 and fitting of the treatment instrument stopper 1e in the channel opening 6 of the treatment instrument insertion channel 7 will be described.

The first stopper section 39 is inserted into the inner circumference portion of the stopper frame 38 from the lower end opening of the stopper frame 38, that is, the opening on the side provided with the flange 46. The first stopper section 39 is formed of a material having elasticity greater than that of the stopper frame 38 and is deformed and contracted to be fitted between the retaining portions 48a and 48b provided in the inner circumference of the stopper frame 38. Alternatively, the first closed film 39a side of the first stopper section 39 may be inserted into the stopper section fitting portion 43 as the upper end opening of the stopper frame 38 and be fitted between the retaining portions 48a and 48b.

The mounting hole 63 of the coupling segment 61 of the second stopper section 40 is fitted and fixed to the attachment part 54 of the stopper frame 38. An arrow-shaped portion 71 of the attachment part 54 is formed to be substantially horizontal to the flange 46. When the operator attaches the second stopper section 40 to the attachment part 54, the mounting hole 63 is hardly deformed in the upper and lower directions, that is, in the direction of the flange 46. The second stopper section 40 can be smoothly fitted without being obstructed by the flange 46. The second stopper section 40 is formed of a material having great elasticity like the first stopper section 39. The removal unit 57 can be inserted into the stopper section fitting portion 43 of the stopper frame 38 by bending the coupling segment 61. When the removal unit 57 is inserted into the stopper section fitting portion 43 of the stopper frame 38, the second seal 58 of the removal unit 57 is contacted in an air-tight manner with the periphery of the upper end opening of the first stopper section 39 fitted along the inner circumference surface of the stopper frame 38. When the handle 60 is seen from the second closed film 56 side, the handle 60 is arranged to be overlapped with the upper surface of the tab 44 of the stopper frame 38. The second stopper section 40 is fitted between the pair of notched grooves 45a and 45b provided in the stopper frame 38.

Fitting of the thus-assembled treatment instrument stopper 1e in the channel opening 6 provided in the treatment instrument insertion channel 7 of the endoscope 2 will be described. The assembled treatment instrument stopper 1e is packed and is previously sterilized by a gamma ray to be sold. When the treatment instrument stopper 1e is used, it is taken out from the pack to be press inserted from the lower end opening of the stopper frame 38, that is, the opening on the side provided with the flange 46, into the channel opening 6 of the treatment instrument insertion channel 7. A flange is formed in the outer circumference of the upper end wall 42 of the stopper frame 38. The treatment instrument stopper 1e can be easily pressed by the fingers when inserted into the channel opening 6 of the treatment instrument insertion channel 7. The lower end opening of the stopper frame 38 passes over the flanged mouth provided in the channel opening 6 by the tilted surface 20 of the engagement portion 49. The mouth is fitted between the engagement portion 49 and the first seal 53a of the lower end opening of the first stopper section 39. The first seal 53a of the first stopper section 39 is contacted in an air-tight manner with the flanged mouth of the channel opening 6 (the state shown in FIG. 22). Without the first seal 53a, the channel opening 6 may be sealed to the stopper frame 38. In these states, the stopper frame 38 contacted with the channel opening 6 may be rotated or cannot be rotated.

In the state where the treatment instrument stopper 1e is fitted in the channel opening 6 of the treatment instrument insertion channel 7 and the second stopper section 40 is fitted in the stopper section fitting portion 43 of the stopper frame 38, the distal end portion of the treatment instrument 5, not shown, is passed into the second treatment instrument insertion hole 55 provided in the second closed film 56 of the second stopper section 40 of the treatment instrument stopper 1e. Then, the treatment instrument 5 is continuously inserted from the second treatment instrument insertion hole 55 through the first treatment instrument insertion hole 41 provided in the first closed film 39a of the first stopper section 39 into the treatment instrument insertion channel 7.

The second treatment instrument insertion hole 55 of the second stopper section 40 and the first treatment instrument insertion hole 41 of the first stopper section 39 are contacted with the outer circumference of the treatment instrument 5 for insertion. The sealed state of the treatment instrument insertion channel 7 can be secured. If contaminants and air in the body cavity are flowed backward through the treatment instrument insertion channel 7, the first closed film 39a and the slit formed in the second treatment instrument insertion hole 55 can prevent contaminants and air in the body cavity from being leaked to the outside from the channel opening 6.

The stopper frame 38 is formed of a material harder than that of the second stopper section 40. When the second stopper section 40 is fitted in the stopper section fitting portion 43, the stopper frame 38 is not deformed. In this embodiment, in the state where the second stopper section 40 is fitted in the stopper section fitting portion 43, the size is previously set by being formed by the pitch of the distance X. With allowance for a press stroke when the second stopper section 40 is fitted in the stopper section fitting portion 43, the second stopper section 40 can be easily fitted.

When the treatment instrument 5 having a very large outer diameter is used, the advance or retreat force amount of the insertion operation can be large due to the contacted state of the first closed film 39a and the slit formed in the second treatment instrument insertion hole 55. In such case, the second stopper section 40 is removed from the stopper frame 38 (the state shown in FIG. 24) and the treatment instrument 5 can be inserted only into the first treatment instrument insertion hole 41 of the stopper frame 38. The sealed state of the treatment instrument insertion channel 7 can be secured and the advance or retreat force amount of the insertion operation of the treatment instrument 5 having a very large outer diameter can be smaller. When the treatment instrument 5 having a large outer diameter is used, the insertion ability of the treatment instrument 5 having the second stopper section 40 fitted in the stopper section fitting portion 43 is compared with that of the treatment instrument 5 having the second stopper section 40 removed from the stopper section fitting portion 43. As the outer diameter of the treatment instrument 5 is larger, the good insertion ability of the treatment instrument 5 having the second stopper section 40 removed from the stopper section fitting portion 43 becomes significant.

When the removal unit 57 of the second stopper section 40 is removed from the stopper section fitting portion 43 of the stopper frame 38, the handle 60 is held and pulled up. The handle 60 provided in the second stopper section 40 is disposed to be upper than the tab 44 provided in the stopper frame 38 used for removing the removal unit 57 by collapsing the stopper frame 38, that is, in the position in which the distance from the channel opening 6 to the handle 60 is longer than that from the channel opening 6 to the tab 44. The handle 60 is formed to be longer than the tab 44 and to have a held area larger than that of the tab 44. The pitch between the handle 60 and the tab 44 toward the distal end of the handle 60 is formed to be larger than that on the proximal end of the handle 60. The removal unit 57 of the second stopper section 40 can be removed from the stopper section fitting portion 43 without engaging the fingers onto the tab 44 by mistake. The pullup operation of the handle 60 can be easily done by engaging the finger onto the convexes 59 provided on the handle 60. The handle 60 is formed of a material softer than that of the tab 44. When the removal unit 57 of the second stopper section 40 is removed from the stopper section fitting portion 43 of the stopper frame 38 by the pullup operation of the handle 60 and the operator touches the tab 44 by mistake, the operator can easily recognize by the difference in hardness that it is not the handle 60.

The longitudinal direction of the forming direction of the slit hole of the second treatment instrument insertion hole 55 formed in the second stopper section 40 is substantially equal to the direction removing the second stopper section 40 from the stopper section fitting portion 43 provided in the stopper frame 38. When the removal unit 57 of the second stopper section 40 is removed from the stopper section fitting portion 43, a force is reliably transmitted to the removal unit 57 and the second stopper section 40 can be easily removed. When the treatment instrument is not used, the slit of the second treatment instrument insertion hole 55 formed in the second stopper section 40 can prevent contaminants and air in the body cavity from being leaked to the outside.

Figure 24:
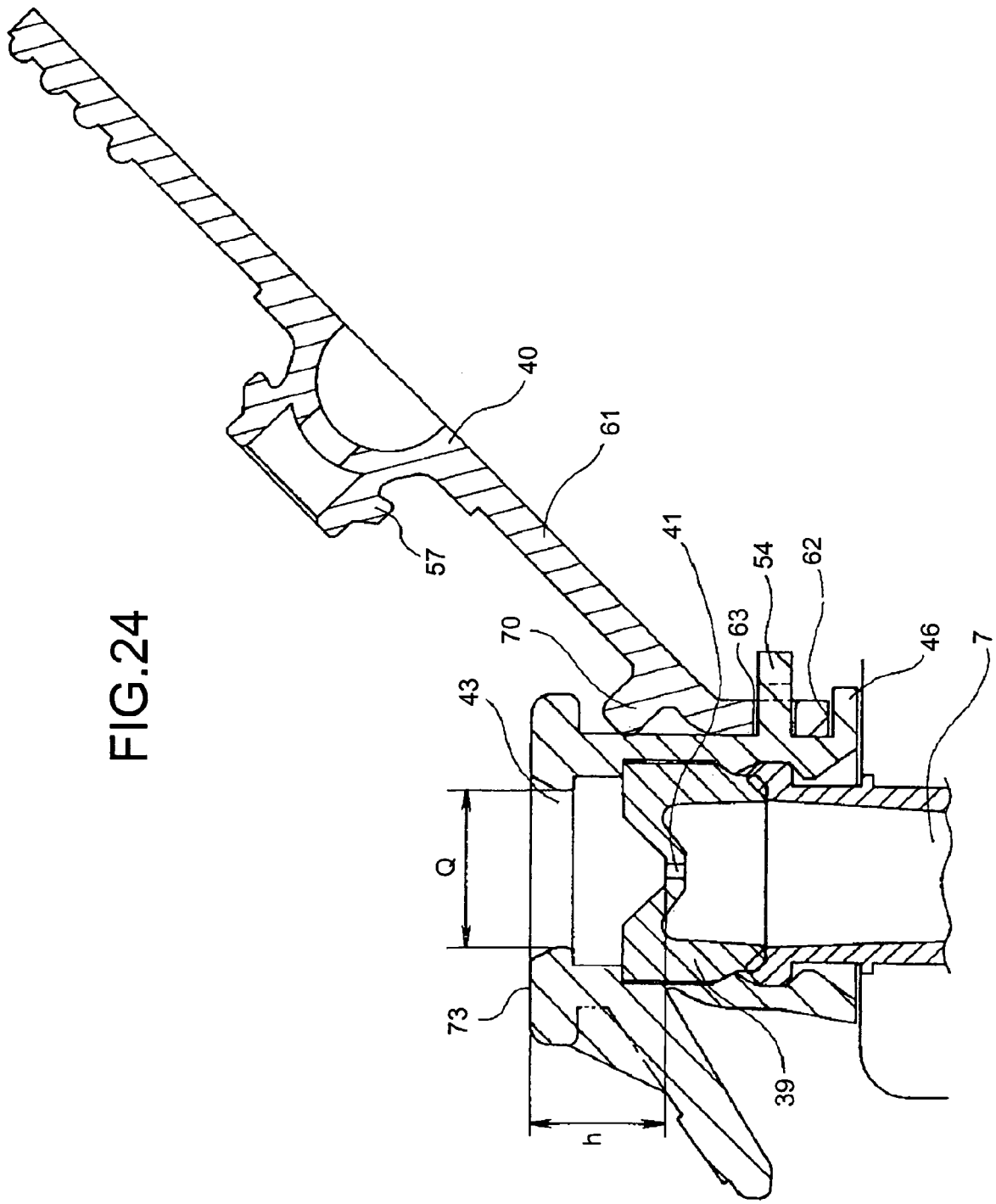
FIG. 24 is a cross-sectional view of the treatment instrument stopper according to the sixth embodiment of the endoscope treatment instrument stopper according to the present invention in which the stopper section is removed from the state of FIG. 22.

In the second stopper section 40, the coupling segment 61 formed integrally with the removal unit 57 has the function of exerting the removal unit 57 in the direction moved away from the stopper section fitting portion 43 when the removal unit 57 is removed from the stopper section fitting portion 43 provided in the stopper frame 38. Specifically, the coupling segment 61 is formed to be extended in the direction in parallel with the outer surface of the stopper frame 38 near the mounting hole 63 fixed onto the outer surface of the stopper frame 38 and is provided with the support portion 70 in a convex shape on the surface opposite the outer surface of the stopper frame 38. When the second stopper section 40 removed from the stopper section fitting portion 43 of the stopper frame 38 is released, it is hung along the outside of the stopper frame 38 by the support portion 70. The second stopper section 40 is moved away from the projected region Q of the stopper section fitting portion 43 of the stopper frame 38 (FIG. 24). When the treatment instrument 5 is directly inserted into the stopper section fitting portion 43 of the stopper frame 38 and the first treatment instrument insertion hole 41 of the first stopper section 39, the second stopper section 40 cannot obstruct the insertion operation. In addition, when the second stopper section 40 removed from the stopper frame 38 is released, it is hardly shaken in the right and left directions and is hung along the outside of the stopper frame 38. The second stopper section 40 can be easily fitted in the stopper section fitting portion 43 again.

As various treatments using the endoscope 2, water supply mainly for cleaning of a diseased portion and check of a blood point can be performed using a syringe as the treatment instrument 5. In this embodiment, when the syringe is inserted from the second treatment instrument insertion hole 55 into the first treatment instrument insertion hole 41 for use in the state where the second stopper section 40 is fitted in the stopper section fitting portion 43 of the stopper frame 38, the distance H from the opening of the second treatment instrument insertion hole 55 to the opening of the first treatment instrument insertion hole 41 is set to 9 mm or less so as to reliably perform water supply from the syringe into the treatment instrument insertion channel 7. The shape and length of the distal end of the syringe are almost the same as those of any syringe of various sizes. The distal end of the syringe always passes over the first treatment instrument insertion hole 41. The syringe as the treatment instrument 5 inserted into the first treatment instrument insertion hole 41 can reliably perform treatment such as water supply into the treatment instrument insertion channel 7.

In the state where the second stopper section 40 is fitted in the stopper section fitting portion 43 of the stopper frame 38, the inner surface 72 and the upper surface 73 of the stopper section fitting portion 43 are covered by the second stopper section 40 formed of an elastic body. The first stopper section 39 is brought into contact with the second stopper section 40 so as to connect the first treatment instrument insertion hole 41 to the second treatment instrument insertion hole 55. When the syringe is fitted as the treatment instrument 5, it cannot be directly contacted with the stopper frame 38 formed of a material harder than that of the second stopper section 40. When water supply is performed so as to slightly activate the syringe, no extra stress is applied to the edge of the syringe inserted into the second treatment instrument insertion hole 55 so that the syringe cannot be collapsed.

In the state where the second stopper section 40 is not fitted in the stopper section fitting portion 43 of the stopper frame 38, when the syringe is used as the treatment instrument 5, the distance h from the upper surface 73 as the end surface of the stopper section fitting portion of the stopper frame 38 to the opening of the first treatment instrument insertion hole 41 is set to 9 mm or less. In this state, the edge of the syringe always passes over the first treatment instrument insertion hole 41. The syringe as the treatment instrument 5 inserted into the first treatment instrument insertion hole 41 can reliably perform treatment such as water supply into the treatment instrument insertion channel 7.

The operation removing the treatment instrument stopper 1e from the channel opening 6 of the treatment instrument insertion channel 7 will be described. When the treatment instrument stopper 1e is removed from the channel opening 6, the tab 44 provided in the stopper frame 38 is held to pull up the held tab 44 in the direction indicated by the index 47 (the direction of P in FIG. 18). By the pullup operation of the tab 44, the stopper frame 38 is torn from the side surface provided with the tab 44 of the stopper frame 38 along the pair of notched grooves 45a and 45b provided in the stopper frame 38 via the upper end wall 42 toward the side surface of the stopper frame 38 opposite the location provided with the tab 44. In this state, the stopper frame 38 is divided in half and can be easily removed from the channel opening 6. The treatment instrument stopper 1e can be removed in the non-reusable state by the torn stopper frame 38.

The second stopper section 40 is held at both sides in the state where it covers a part of the notched grooves 45a and 45b and cannot cross over the notched grooves 45a and 45b. The removing operation of the treatment instrument stopper 1e can be performed only by the pullup operation of the tab 44 without removing the removal unit 57 of the second stopper section 40 from the stopper section fitting portion 13.

The flange 46 is formed at the lower end of the side surface of the stopper frame 38 opposite the side surface provided with the tab 44. When the pullup operation of the tab 44 is performed, the stopper frame 38 can be reliably torn along the pair of notched grooves 45a and 45b in the state where the base of the stopper frame 38 is stable. The folding force amount of the tab 44 is larger than the removing force amount when the second stopper section 40 is removed from the stopper section fitting portion 43 by holding the handle 60. The operation removing the second stopper section 40 from the stopper section fitting portion 43 by holding the handle 60 prevents the stopper frame 38 from being collapsed first.

The rib 75 is formed on the side in the direction performing the pullup operation of the tab 44. When the stopper frame 38 is attached to the channel opening 6 and the tab 44 is operated in a V direction opposite the P direction by mistake, a force is hard to apply to the notched grooves 45a and 45b. The pair of notched grooves 45a and 45b provided on the back side of the tab 44 cannot be easily torn.

The first stopper section 39 and the second stopper section 40 can be assembled by simple pressing into the stopper frame 38. Automatic assembling by machining can be done. The efficiency of the assembling operation can be improved.

Figure 25:
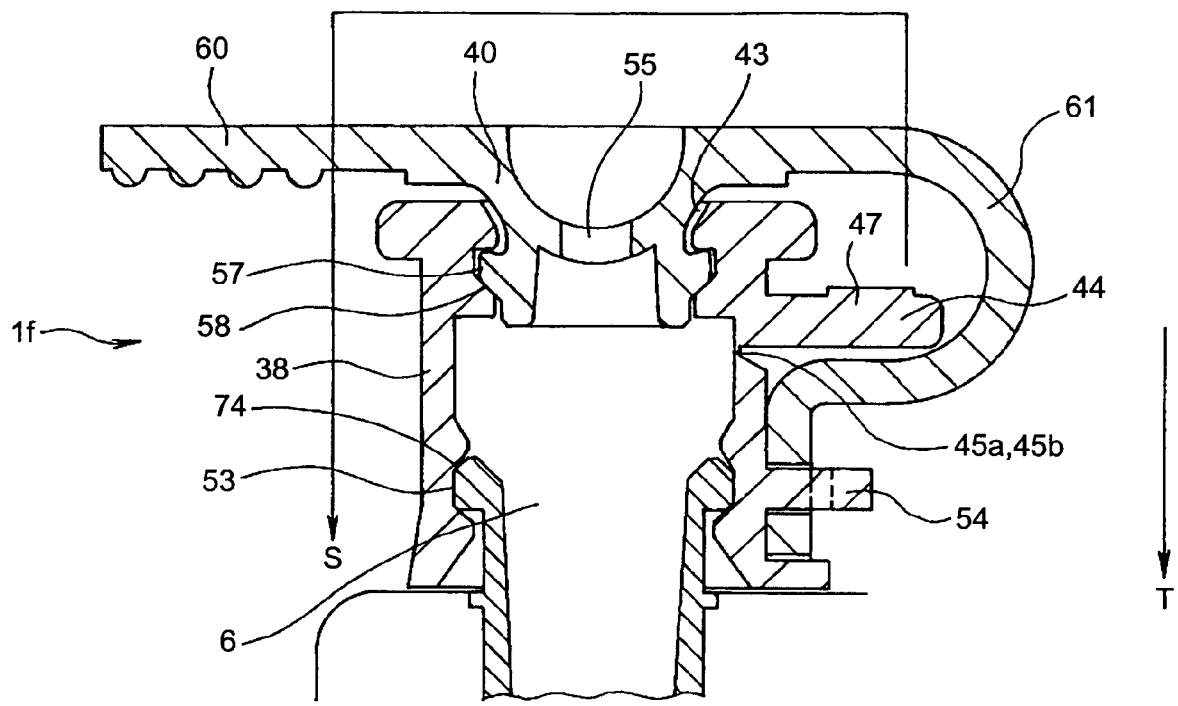
FIG. 25 is a side view of an endoscope treatment instrument stopper according to a seventh embodiment of the present invention.
Figure 26:
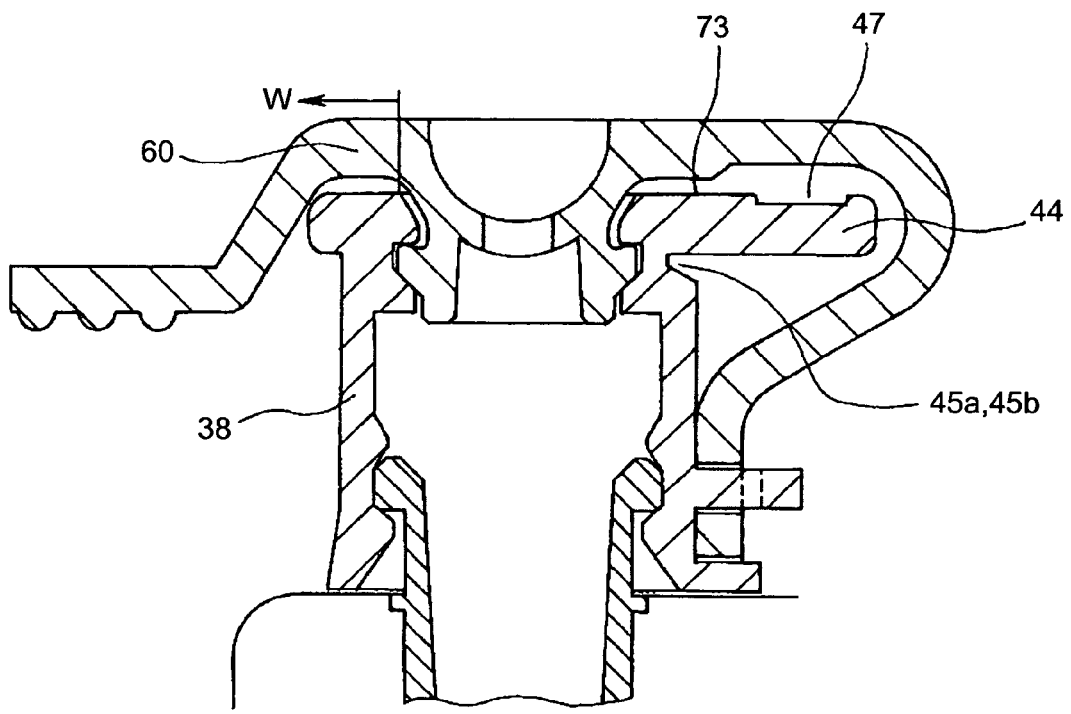
FIG. 26 is a side view showing another constructional example of FIG. 25 of the endoscope treatment instrument stopper according to the seventh embodiment of the present invention.

A seventh embodiment of a treatment instrument stopper according to the present invention will be described using FIGS. 25 and 26. The same portions as those of FIG. 1 to 24 are represented by like reference numerals and the detailed description is omitted.

A treatment instrument stopper 1f of the seventh embodiment is different from the treatment instrument stopper 1e of the sixth embodiment in that the position of the tab 44 is different. The tab 44 of the treatment instrument stopper 1f of the seventh embodiment is extended horizontally from a part of the outer circumference surface on the same side as the attachment part 54 provided in the stopper frame 38. The tab 44 is provided on the side lower than the handle 60 of the second stopper section 40, that is, in the position in which the distance from the tab 44 to the channel opening 6 is short in the state where the stopper frame 38 is fitted in the channel opening 6 and the second stopper section 40 is fitted in the stopper section fitting portion 43. In the description of the sixth embodiment, the handle 60 is formed to be extended in the outside direction of the second closed film 56 on the extension line in the direction forming the slit hole of the stopper section fitting portion 43, that is, in the direction indicated by the W portion in FIG. 22. In the seventh embodiment, as shown in FIG. 26, a part of the handle 60 may be largely deformed midway in the lower direction, that is, in the direction in which the distance from a part of the handle 60 to the channel opening 6 is short. The index 47 provided in the tab 44 may be in a concave shape as shown in FIG. 26 because automatic assembling by machining can prevent damage due to ultrasonic vibration in movement in the parts feeder. The treatment instrument stopper 1f of the seventh embodiment is not provided with the first stopper section 39.

In the above-described construction, when the second stopper section 40 is fitted in the stopper section fitting portion 43 of the stopper frame 38, the coupling segment 61 covers the upper and lower directions of the tab 44, that is, the axial direction of the treatment instrument insertion channel 7 of the channel opening 6. The operation direction of the tab 44 when the stopper frame 38 is removed from the channel opening 6 is different from that of the sixth embodiment and is an S direction shown in FIG. 25. The notched grooves 45a and 45b are formed on the upper side (the lower side in FIG. 25) of the tab 44. The operation direction of the tab 44 may be a T direction shown in FIG. 25.

The first seal 53 of this embodiment is a portion formed by the stopper frame 38 and a venting cap 74 provided in the channel opening 6 when the stopper frame 38 is fitted in the channel opening 6. The second seal 58 of this embodiment is a portion formed by the stopper frame 38 and the removal unit 57 when the second stopper section 40 is fitted in the stopper frame 38.

The treatment instrument stopper 1f of this embodiment is not provided with the first stopper section 39 provided in the treatment instrument stopper 1e of the sixth embodiment. In the state where the treatment instrument stopper 1e is fitted in the channel opening 6 of the treatment instrument insertion channel 7 and that the second stopper section 40 is fitted in the stopper section fitting portion 43 of the stopper frame 38, the distal end of the treatment instrument 5, not shown, is passed into the second treatment instrument insertion hole 55 provided in the second closed film 56 of the second stopper section 40 of the treatment instrument stopper 1e. Then, the treatment instrument 5 is inserted from the second treatment instrument insertion hole 55 through the inside of the stopper frame 38 into the treatment instrument insertion channel 7.

The insertion operation is performed in the state where the second treatment instrument insertion hole 55 of the second stopper section 40 is contacted with the outer circumference of the treatment instrument 5. The contacted state of the treatment instrument insertion channel 7 can be secured. If contaminants and air in the body cavity are flowed backward through the treatment instrument insertion channel 7, the slit formed in the second treatment instrument insertion hole 55 can prevent contaminants and air in the body cavity from being leaked out to the outside from the channel opening 6.

The treatment instrument stopper 1f of this embodiment is not provided with the first stopper section 39 provided in the treatment instrument stopper 1e of the sixth embodiment. When the treatment instrument 5 having a very large outer diameter is used in the state where the second stopper section 40 is removed from the stopper section fitting portion 43 of the stopper frame 38, insertion of the treatment instrument 5 can be performed more lightly than the treatment instrument stopper 1e of the sixth embodiment. When the treatment instrument 5 having a very large outer diameter is used, the insertion ability of the treatment instrument 5 having the second stopper section 40 fitted in the stopper section fitting portion 43 is compared with that of the treatment instrument 5 having the second stopper section 40 removed from the stopper section fitting portion 43. As the outer diameter of the treatment instrument 5 is larger, the good insertion ability of the treatment instrument 5 having the second stopper section 40 removed from the stopper section fitting portion 43 becomes significant.

When the treatment instrument 5 having a very large outer diameter is used in the state where the second stopper section 40 is removed from the stopper section fitting portion 43, the treatment instrument stopper 1f of this embodiment is not provided with the first stopper section 39 provided in the treatment instrument stopper 1e of the sixth embodiment. Contaminants and air in the body cavity can be easily slightly leaked. As the outer diameter of the treatment instrument 5 is larger, the clearance of the inner wall portion of the treatment instrument insertion channel 7 and the outer surface portion of the treatment instrument 5 is smaller. The amount of contaminants and air in the body cavity leaked from the channel opening 6 is relatively small.

When the syringe is used as the treatment instrument 5, in the state where the second stopper section 40 is fitted in the stopper section fitting portion 43 of the stopper frame 38, the distal end portion of the syringe reaches the inside of the treatment instrument insertion channel 7 to reliably perform treatment such as water supply.

The operation removing the treatment instrument stopper 1f from the channel opening 6 of the treatment instrument insertion channel 7 will be described. When the second stopper section 40 is fitted in the stopper section fitting portion 43 of the stopper frame 38, the coupling segment 61 covers the upper and lower directions of the tab 44, that is, the axial direction of the treatment instrument insertion channel 7 of the channel opening 6. In this state, the tab 44 cannot be operated. In this embodiment, when the treatment instrument stopper 1f is removed from the channel opening 6 of the treatment instrument insertion channel 7, the second stopper section 40 is removed from the stopper section fitting portion 43 of the stopper frame 38 so that the tab 44 can be operated. Then, the tab 44 is pulled up in the S direction shown in FIG. 25 to collapse the stopper frame 38 for removing the treatment instrument stopper 1f from the channel opening 6 of the treatment instrument insertion channel 7. In this embodiment, unless the second stopper section 40 is removed from the stopper section fitting portion 43 of the stopper frame 38, the tab 44 cannot be operated. When the second stopper section 40 is removed from the stopper section fitting portion 43 of the stopper frame 38, the frequency of erroneous operation of the tab 44 of the treatment instrument stopper 1f is lower than that of the treatment instrument stopper 1e of the sixth embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope treatment instrument stopper fitted in a channel of an endoscope, comprising:
    a stopper frame fitted into a channel opening, the stopper frame being formed in a substantially cylindrical shape, and having an upper portion and a lower portion;
    a first stopper section inserted into an inner circumference of the cylindrical shape of the stopper frame so that the first stopper section is retained in the inner circumference of the cylindrical shape, independent of the stopper frame, and having a first treatment instrument insertion hole opposite the channel opening through which a treatment instrument is inserted;
    a stopper section fitting portion provided on the upper portion of the cylindrical shape of the stopper frame;
    an engagement portion provided on the lower portion of the cylindrical shape of the stopper frame and fitted in the channel opening;
    a tearing provided on the cylindrical shape of the stopper frame and being capable of tearing the stopper frame when the endoscope treatment instrument stopper is removed from the channel opening;

a tab formed integrally with the upper portion of the stopper frame and causing the tearing to be easily torn when the tab is pulled;

an attachment part provided on the lower portion of the stopper frame;

a second stopper section, independent of the stopper frame, having a second treatment instrument insertion hole into which the treatment instrument is inserted, removably fitted into the stopper section fitting portion of the stopper frame, and formed so that the second treatment instrument insertion hole is opposite the first treatment instrument insertion hole of the first stopper section when the second stopper section is fitted in the stopper section fitting portion;

a coupling segment formed integrally with the second stopper section and having a part connected to the attachment part, the coupling segment exerting the second stopper section in a direction moved away from the stopper section fitting portion when the second stopper section is removed from the stopper section fitting portion; and a handle, provided on the second stopper section and disposed at a position overlapped with a top surface portion of the tab, for removing the second stopper section from the stopper section fitting portion.

2. The endoscope treatment instrument stopper according to claim 1, further comprising protruded retaining portions for fitting and retaining an outer circumference of the first stopper section, formed on the inner circumference surface of a cylindrical middle portion of the stopper frame.

3. The endoscope treatment instrument stopper according to claim 1, wherein the second stopper section fitted in the stopper section fitting portion is held at both ends without passing over the tearing of the stopper frame.

4. The endoscope treatment instrument stopper according to claim 1, wherein the tab is used for removing the stopper frame provided in a position where a distance from the channel opening to the tab is shorter than that from the channel opening to the handle in a state where the stopper section is fitted in the stopper frame and the stopper frame is fitted in the channel opening.

5. The treatment instrument stopper section according to claim 1, wherein the attachment part is fixed to the stopper frame so that an extension direction of the coupling segment is a direction in parallel with an outer surface of the stopper frame at least near the attachment part, and the coupling segment exerts the removal unit in the direction moved away from the stopper section fitting portion by a support portion in a convex shape formed on a surface opposite the outer surface of the stopper frame.

* * * * *